(12) United States Patent
Rodriguez et al.

(10) Patent No.: US 8,251,696 B2
(45) Date of Patent: Aug. 28, 2012

(54) AESTHETIC ORTHODONTIC BRACKET AND METHOD OF MAKING SAME

(75) Inventors: Rodolfo Rodriguez, Mira Loma, CA (US); Farrokh Farzin-Nia, Inglewood, CA (US)

(73) Assignee: Ormco Corporation, Orange, CA (US)

(*) Notice: Subject to any disclaimer, the term of this patent is extended or adjusted under 35 U.S.C. 154(b) by 143 days.

(21) Appl. No.: 12/540,638

(22) Filed: Aug. 13, 2009

(65) Prior Publication Data

US 2010/0055637 A1 Mar. 4, 2010

Related U.S. Application Data

(60) Provisional application No. 61/088,519, filed on Aug. 13, 2008, provisional application No. 61/106,358, filed on Oct. 17, 2008.

(51) Int. Cl.
*A61C 3/00* (2006.01)
(52) U.S. Cl. ......................................................... 433/10
(58) Field of Classification Search ................... 433/8, 9, 433/10, 11, 12, 201.1; 29/896.1–896.11; 264/648, 649; 501/103, 120, 127
See application file for complete search history.

(56) References Cited

U.S. PATENT DOCUMENTS

| | | | |
|---|---|---|---|
| 3,504,438 A | 4/1970 | Wittman et al. | |
| 4,050,156 A | 9/1977 | Chasanoff et al. | |
| 4,077,126 A | 3/1978 | Pletcher | |
| 4,107,844 A | 8/1978 | Kurz | |
| 4,180,912 A | 1/1980 | Kesling | |
| 4,209,906 A | 7/1980 | Fujita | |
| 4,216,583 A | 8/1980 | Reynolds | |
| 4,219,617 A | 8/1980 | Wallshein | |

(Continued)

FOREIGN PATENT DOCUMENTS

CA 1326382 C 1/1994

(Continued)

OTHER PUBLICATIONS

Ishitobi, Fabrication of Translucent Al2O3 by High Pressure Sintering, Institute of Scientific and Industrial Research, 1977, vol. 56, No. 6.*

(Continued)

*Primary Examiner* — Cris L Rodriguez
*Assistant Examiner* — Eric Rosen
(74) *Attorney, Agent, or Firm* — Wood, Herron & Evans, LLP

(57) ABSTRACT

An orthodontic bracket for coupling an archwire with a tooth includes a bracket body that has an archwire slot adapted to receive the archwire. A movable member is engaged with the bracket body and is movable between an opened position and a closed position. The bracket body and the movable member may be made from a transparent or translucent polycrystalline ceramic for improved aesthetics. The polycrystalline ceramic has a grain size distribution characterized by an average grain size in the range of larger than 3.4 μm to about 6 μm. The polycrystalline ceramic may have a fracture toughness of at least 4.0 MPa·m1/2. The grain size distribution may not be characterized as a lognormal distribution and may be a multimodal distribution. The polycrystalline ceramic may comprise aluminum oxide or alumina. The grain size distribution may be characterized by having up to about 50% of the grains being less than about 3 μm in size. The grain size distribution may be characterized by having up to about 90% of the grains being less than about 10 μm in size.

16 Claims, 23 Drawing Sheets

U.S. PATENT DOCUMENTS

| | | | |
|---|---|---|---|
| 4,242,085 A | 12/1980 | Wallshein | |
| 4,310,306 A | 1/1982 | Wallshein | |
| 4,322,206 A | 3/1982 | Reynolds | |
| 4,595,598 A | 6/1986 | De Luca et al. | |
| 4,626,209 A | 12/1986 | Tsai et al. | |
| 4,639,218 A | 1/1987 | Jones et al. | |
| 4,669,980 A | 6/1987 | Degnan | |
| 4,674,978 A | 6/1987 | Acevedo | |
| 4,681,538 A | 7/1987 | DeLuca et al. | |
| 4,698,017 A | 10/1987 | Hanson | |
| 4,780,079 A | 10/1988 | Kato et al. | |
| 4,784,606 A | 11/1988 | Jones et al. | |
| 4,789,649 A | 12/1988 | Abert et al. | |
| 4,799,882 A | 1/1989 | Kesling | |
| 4,820,545 A | 4/1989 | Negrych | |
| 4,826,430 A | 5/1989 | Chen et al. | |
| 4,838,786 A | 6/1989 | Reher et al. | |
| 4,842,512 A | 6/1989 | Kesling | |
| 4,846,681 A | 7/1989 | Mourany et al. | |
| 4,859,179 A | 8/1989 | Kesling | |
| 4,877,398 A | 10/1989 | Kesling | |
| 4,878,840 A | 11/1989 | Reynolds | |
| 4,902,224 A | 2/1990 | Collins et al. | |
| 4,915,625 A | 4/1990 | Tsukuma et al. | |
| 4,927,360 A | 5/1990 | Pospisil | |
| 4,932,865 A | 6/1990 | Collins et al. | |
| 4,936,773 A | 6/1990 | Kawaguchi | |
| 4,946,387 A | 8/1990 | Adell | |
| 4,948,366 A | 8/1990 | Horn et al. | |
| 4,954,080 A | 9/1990 | Kelly et al. | |
| 4,968,459 A | 11/1990 | Sernetz | |
| 4,988,293 A | 1/1991 | Collins et al. | |
| 5,011,403 A | 4/1991 | Sadoun et al. | |
| 5,011,410 A | 4/1991 | Culler et al. | |
| 5,022,854 A | 6/1991 | Broughton et al. | |
| 5,030,089 A | 7/1991 | Kawaguchi | |
| 5,032,081 A | 7/1991 | Farzin-Nia et al. | |
| 5,044,945 A | 9/1991 | Peterson | |
| 5,061,183 A | 10/1991 | Nicholson | |
| 5,064,369 A | 11/1991 | Kawaguchi | |
| 5,064,370 A | 11/1991 | Jones | |
| 5,066,225 A | 11/1991 | Forbes Jones et al. | |
| 5,067,897 A | 11/1991 | Tuneberg | |
| 5,071,344 A | 12/1991 | Wong et al. | |
| 5,074,783 A | 12/1991 | Reher | |
| 5,078,596 A | 1/1992 | Carberry et al. | |
| 5,094,614 A | 3/1992 | Wildman | |
| 5,098,288 A | 3/1992 | Kesling | |
| 5,108,285 A | 4/1992 | Tuneberg | |
| 5,109,586 A | 5/1992 | Jones et al. | |
| 5,110,290 A | 5/1992 | Wong | |
| 5,125,832 A | 6/1992 | Kesling | |
| 5,126,094 A | 6/1992 | Farzin-Nia et al. | |
| 5,147,202 A | 9/1992 | Masuhara et al. | |
| 5,154,607 A | 10/1992 | Hanson | |
| 5,158,452 A | 10/1992 | Franseen et al. | |
| 5,161,969 A | 11/1992 | Pospisil et al. | |
| 5,183,403 A | 2/1993 | Masuhara et al. | |
| 5,197,873 A | 3/1993 | Wong et al. | |
| 5,203,804 A | 4/1993 | Nikutowski et al. | |
| 5,219,283 A | 6/1993 | Farzin-Nia et al. | |
| 5,219,805 A | 6/1993 | Yoshida et al. | |
| 5,231,062 A | 7/1993 | Mathers et al. | |
| 5,242,298 A | 9/1993 | Sernetz | |
| 5,242,299 A | 9/1993 | Yoshida | |
| 5,252,066 A | 10/1993 | Fairhurst | |
| 5,254,002 A | 10/1993 | Reher et al. | |
| 5,256,062 A | 10/1993 | Griott | |
| 5,263,858 A | 11/1993 | Yoshida et al. | |
| 5,263,859 A | 11/1993 | Kesling | |
| 5,269,680 A | 12/1993 | Kawaguchi | |
| 5,302,116 A | 4/1994 | Viazis | |
| 5,322,435 A | 6/1994 | Pletcher | |
| 5,356,288 A | 10/1994 | Cohen | |
| 5,358,402 A | 10/1994 | Reed et al. | |
| 5,362,232 A | 11/1994 | Franseen et al. | |
| 5,366,372 A | 11/1994 | Hansen et al. | |
| 5,374,187 A | 12/1994 | Vashi et al. | |
| 5,380,196 A | 1/1995 | Kelly et al. | |
| 5,429,500 A | 7/1995 | Damon | |
| 5,439,379 A | 8/1995 | Hansen | |
| 5,441,408 A | 8/1995 | Moschik | |
| 5,466,151 A | 11/1995 | Damon | |
| 5,470,228 A | 11/1995 | Franseen et al. | |
| 5,474,445 A | 12/1995 | Voudouris | |
| 5,474,446 A | 12/1995 | Wildman et al. | |
| 5,484,716 A | 1/1996 | Katsumata et al. | |
| 5,541,408 A | 7/1996 | Sittler | |
| 5,575,644 A | 11/1996 | Tuneburg | |
| 5,595,484 A | 1/1997 | Orikasa et al. | |
| 5,607,301 A | 3/1997 | Roman | |
| 5,613,850 A | 3/1997 | Wildman et al. | |
| 5,618,174 A | 4/1997 | Mors | |
| 5,618,175 A | 4/1997 | Reher et al. | |
| 5,630,715 A | 5/1997 | Voudouris | |
| 5,653,588 A | 8/1997 | Moschik | |
| 5,656,564 A | 8/1997 | Nakayama et al. | |
| 5,681,165 A | 10/1997 | Feldman | |
| 5,692,896 A | 12/1997 | Pospisil et al. | |
| 5,707,231 A * | 1/1998 | Watt et al. | 433/8 |
| 5,716,208 A | 2/1998 | Forman | |
| 5,746,594 A | 5/1998 | Jordan et al. | |
| RE35,863 E | 7/1998 | Sachdeva et al. | |
| 5,782,631 A | 7/1998 | Kesling et al. | |
| 5,795,151 A | 8/1998 | Nonami et al. | |
| 5,813,852 A | 9/1998 | Kawaguchi | |
| 5,816,801 A | 10/1998 | Farzin-Nia et al. | |
| 5,854,158 A * | 12/1998 | Nawa et al. | 501/104 |
| 5,857,850 A | 1/1999 | Voudouris | |
| 5,863,199 A | 1/1999 | Wildman | |
| 5,906,486 A | 5/1999 | Hanson | |
| 5,908,293 A | 6/1999 | Voudouris | |
| 5,911,574 A | 6/1999 | Casey | |
| 5,913,680 A | 6/1999 | Voudouris | |
| 5,931,667 A | 8/1999 | Papandreas | |
| 5,931,668 A | 8/1999 | Birkel | |
| 5,944,517 A | 8/1999 | Binder | |
| 6,068,473 A | 5/2000 | Birkel | |
| 6,071,118 A | 6/2000 | Damon | |
| 6,071,119 A | 6/2000 | Christoff et al. | |
| 6,071,120 A | 6/2000 | Birkel | |
| 6,090,867 A | 7/2000 | Starling, Jr. et al. | |
| 6,142,775 A | 11/2000 | Hansen et al. | |
| 6,168,428 B1 | 1/2001 | Voudouris | |
| 6,193,508 B1 | 2/2001 | Georgakis | |
| 6,203,318 B1 | 3/2001 | Birkel | |
| 6,247,923 B1 | 6/2001 | Vashi | |
| 6,257,883 B1 | 7/2001 | Voudouris | |
| 6,267,590 B1 | 7/2001 | Barry et al. | |
| 6,299,438 B1 | 10/2001 | Sahagian et al. | |
| 6,305,932 B1 | 10/2001 | Mottate | |
| 6,325,622 B1 | 12/2001 | Kelly et al. | |
| 6,368,105 B1 | 4/2002 | Voudouris et al. | |
| 6,394,798 B1 | 5/2002 | Huff et al. | |
| 6,485,299 B1 | 11/2002 | Wildman | |
| 6,540,511 B1 | 4/2003 | Cavaf | |
| 6,554,612 B2 | 4/2003 | Georgakis et al. | |
| 6,607,383 B2 | 8/2003 | Abels et al. | |
| 6,616,445 B2 | 9/2003 | Abels et al. | |
| 6,632,088 B2 | 10/2003 | Voudouris | |
| 6,644,968 B2 | 11/2003 | Orikasa et al. | |
| 6,648,638 B2 | 11/2003 | Castro et al. | |
| 6,659,766 B2 | 12/2003 | Abels et al. | |
| 6,685,468 B1 | 2/2004 | Kesling | |
| 6,695,612 B2 | 2/2004 | Abels et al. | |
| 6,733,285 B2 | 5/2004 | Puttler et al. | |
| 6,733,286 B2 | 5/2004 | Abels et al. | |
| 6,746,242 B1 | 6/2004 | Kesling | |
| 6,786,720 B1 | 9/2004 | Kesling et al. | |
| 6,799,966 B1 | 10/2004 | Horn et al. | |
| 6,846,178 B2 | 1/2005 | Freeman, Jr. et al. | |
| 6,866,505 B2 | 3/2005 | Senini | |
| 6,878,456 B2 | 4/2005 | Castro et al. | |
| 6,932,597 B2 | 8/2005 | Abels et al. | |
| 6,939,133 B2 | 9/2005 | Voudouris | |
| 6,960,079 B2 | 11/2005 | Brennan et al. | |
| 6,964,565 B2 | 11/2005 | Abels et al. | |

| | | |
|---|---|---|
| 6,984,261 B2 | 1/2006 | Cummings et al. |
| 7,014,460 B2 | 3/2006 | Lai et al. |
| 7,022,173 B2 | 4/2006 | Cummings et al. |
| 7,025,591 B1 | 4/2006 | Kesling |
| 7,063,529 B2 | 6/2006 | Abels et al. |
| 7,063,530 B2 | 6/2006 | Abels et al. |
| 7,118,373 B2 | 10/2006 | Abels et al. |
| 7,131,836 B1 | 11/2006 | Kesling |
| 7,140,875 B2 | 11/2006 | Lai et al. |
| 7,140,876 B2 | 11/2006 | Cinader et al. |
| 7,153,130 B2 | 12/2006 | Christoff |
| 7,175,428 B2 | 2/2007 | Nicholson |
| 7,175,833 B1 | 2/2007 | Algar |
| 7,186,115 B2 | 3/2007 | Goldberg et al. |
| 7,192,274 B2 | 3/2007 | Stadtmiller et al. |
| 7,210,927 B2 | 5/2007 | Abels et al. |
| 7,214,057 B2 | 5/2007 | Voudouris |
| 7,217,124 B2 | 5/2007 | Cinader, Jr. et al. |
| 7,217,125 B2 | 5/2007 | Lai et al. |
| 7,234,936 B2 | 6/2007 | Lai et al. |
| 7,247,018 B2 | 7/2007 | Freeman, Jr. et al. |
| 7,247,019 B2 | 7/2007 | Abels et al. |
| 7,255,557 B2 | 8/2007 | Forster |
| 7,264,468 B1 | 9/2007 | Kesling et al. |
| 7,267,545 B2 | 9/2007 | Oda |
| 7,306,457 B2 | 12/2007 | Vigolo |
| 7,323,160 B2 | 1/2008 | Algar et al. |
| 7,326,051 B2 | 2/2008 | Miller |
| 7,331,782 B2 | 2/2008 | Andreiko |
| 7,333,874 B2 | 2/2008 | Taub et al. |
| 7,335,020 B2 | 2/2008 | Castner et al. |
| 7,344,771 B2 | 3/2008 | Kubo et al. |
| 7,361,216 B2 | 4/2008 | Kangas et al. |
| 7,367,800 B2 | 5/2008 | Lai et al. |
| 7,888,279 B2 | 2/2011 | Tsukuma et al. |
| 2002/0110771 A1 | 8/2002 | Abels et al. |
| 2002/0110773 A1 | 8/2002 | Abels et al. |
| 2002/0110778 A1 | 8/2002 | Abels et al. |
| 2002/0132206 A1 | 9/2002 | Voudouris |
| 2003/0049582 A1 | 3/2003 | Abels et al. |
| 2003/0165790 A1 | 9/2003 | Castro et al. |
| 2004/0043204 A1 | 3/2004 | Nair et al. |
| 2004/0063059 A1 | 4/2004 | Meckel |
| 2004/0072117 A1 | 4/2004 | Farzin-Nia et al. |
| 2004/0072119 A1 | 4/2004 | Voudouris |
| 2004/0086824 A1 | 5/2004 | Kesling |
| 2004/0152034 A1 | 8/2004 | Cummings et al. |
| 2004/0229184 A1 | 11/2004 | Senini |
| 2005/0109060 A1 | 5/2005 | Cummings et al. |
| 2005/0136176 A1 | 6/2005 | Rosenflanz et al. |
| 2005/0186525 A1 | 8/2005 | Abels et al. |
| 2005/0239012 A1 | 10/2005 | Bathen et al. |
| 2006/0003282 A1 | 1/2006 | Nicholson |
| 2006/0008761 A1 | 1/2006 | Allred |
| 2006/0051721 A1 | 3/2006 | Carriere Lluch |
| 2006/0057533 A1 | 3/2006 | McGann |
| 2006/0084025 A1 | 4/2006 | Abels et al. |
| 2006/0154195 A1 | 7/2006 | Mather et al. |
| 2006/0163774 A1 | 7/2006 | Abels et al. |
| 2006/0166158 A1 | 7/2006 | Abels et al. |
| 2006/0166159 A1 | 7/2006 | Abels et al. |
| 2006/0172247 A1 | 8/2006 | Abels et al. |
| 2006/0177790 A1 | 8/2006 | Farzin-Nia et al. |
| 2006/0199137 A1 | 9/2006 | Abels et al. |
| 2006/0210942 A1 | 9/2006 | Pace et al. |
| 2006/0263736 A1 | 11/2006 | Moon |
| 2006/0263737 A1* | 11/2006 | Oda ............................. 433/10 |
| 2006/0269889 A1 | 11/2006 | Voudouris |
| 2006/0269895 A1 | 11/2006 | Voudouris |
| 2007/0009849 A1 | 1/2007 | Wool |
| 2007/0015104 A1 | 1/2007 | Wiechmann et al. |
| 2007/0072143 A1 | 3/2007 | Sommer |
| 2007/0134609 A1 | 6/2007 | Wyllie et al. |
| 2007/0134610 A1 | 6/2007 | Wyllie et al. |
| 2007/0134611 A1 | 6/2007 | Nicholson |
| 2007/0134612 A1 | 6/2007 | Contencin |
| 2007/0141524 A1 | 6/2007 | Brennan et al. |
| 2007/0160949 A1 | 7/2007 | Voudouris |
| 2007/0166658 A1 | 7/2007 | Voudouris |
| 2007/0178422 A1 | 8/2007 | Voudouris |
| 2007/0190478 A1 | 8/2007 | Goldberg et al. |
| 2007/0207435 A1 | 9/2007 | Devanathan |
| 2007/0207436 A1 | 9/2007 | Tan et al. |
| 2007/0224569 A1 | 9/2007 | Oda |
| 2007/0243497 A1 | 10/2007 | Voudouris |
| 2007/0248926 A1 | 10/2007 | Lai et al. |
| 2007/0248928 A1 | 10/2007 | Damon |
| 2007/0259303 A1 | 11/2007 | Tsukuma et al. |
| 2007/0259304 A1 | 11/2007 | Hagelganz et al. |
| 2007/0269762 A1 | 11/2007 | Kim et al. |
| 2007/0275342 A1 | 11/2007 | Oda |
| 2007/0281269 A1 | 12/2007 | Forster |
| 2008/0038683 A1 | 2/2008 | Von Mandach |
| 2008/0044787 A1 | 2/2008 | Cinader et al. |
| 2008/0081309 A1* | 4/2008 | Wyllie et al. ............. 433/8 |
| 2008/0096150 A1 | 4/2008 | Cinader |
| 2008/0113311 A1 | 5/2008 | Forster |
| 2009/0004619 A1 | 1/2009 | Oda et al. |
| 2009/0104578 A1 | 4/2009 | Tsukuma et al. |
| 2009/0111067 A1 | 4/2009 | Tsukuma et al. |

FOREIGN PATENT DOCUMENTS

| | | |
|---|---|---|
| EP | 0430654 | 6/1991 |
| EP | 1070484 A2 | 1/2001 |
| EP | 1787601 A1 | 5/2007 |
| EP | 1836990 | 9/2007 |
| EP | 2055687 | 5/2009 |
| JP | 64052448 U | 2/1989 |
| JP | 2001-029363 | 2/2001 |
| JP | 2005330164 A | 12/2005 |
| JP | 2006-087915 | 4/2006 |
| JP | 2006290688 | 10/2006 |
| JP | 2006-326305 A | 12/2006 |
| RU | 1793576 C | 9/1995 |
| RU | 2110972 C1 | 5/1998 |
| WO | 8908085 A1 | 9/1989 |
| WO | 9729712 A1 | 8/1997 |
| WO | 2005084575 A1 | 9/2005 |
| WO | 2005094715 A1 | 10/2005 |
| WO | 2007115268 | 10/2007 |

OTHER PUBLICATIONS

Invitation to Pay Additional Fees and, Where Applicable, Protest Fee in corresponding PCT Application No. PCT/US2009/053710; Dec. 1, 2009; 7 pages; European Patent Office.

International Search Report and Written Opinion of the International Searching Authority in corresponding PCT/US2009/053710 mailed Jan. 19, 2010, 16 pages.

U.S, Patent and Trademark Office, Office Action in U.S. Appl. No. 12/540,627 dated Feb. 10, 2011.

Japanese Patent Office, Machine translation of Japanese Patent Publication No. 2006-290688, Application No. 2005-114997, Applicant: Tosoh Corp., entitled "Translucent Ceramic," published Oct. 26, 2006, obtained from Japanese Patent Office website on Nov. 21, 2011.

European Patent Office, Office Action in European Patent Application No. 09791489.9, dated Feb. 13, 2012.

U.S. Patent and Trademark Office, Office Action in U.S. Appl. No. 12/617,507 dated Feb. 16, 2012.

Breviary Technical Ceramics—(http://www.nonmet.mat.ethz.ch/education/courses/Materialwissenschaft_2/brevier.pdf)—Published on Sep. 28, 2006 by the Ceramic Industry Association.

Eric H. Jordan and Maurice Gell—"Nano Crystalline Ceramic and Ceramic Coatings Made by Conventional and Solution Plasma Spray"—Published in 2005 in Nanomaterial Technology for Military Vehicle Structural Applications.

A. Quade, H. Wulff, H. Steffen, T.M. Tun, R. Nippier—"Investigation of the aluminum oxidation in an oxygen plasma excited by microwaves."—Published in 2000 Elsevier Science B.V.

Fernando Guibeteau, Nitin P. Padture and Brian R. Lawn—"Effect of Grain Size on Hertzian Contact Damage in Alumina"—Published in J. Am. Cerm. Soc., 77 [7] 1825-31 (1994).

Wei-Chao Gu, Guo-Huan Lv, Huan Chen, Guang-Liang Chen, Wen-Ran Feng, Si-Ze Yang—"Characterisation of ceramic coating produced by plasma electrolytic oxidation of aluminum alloy"—Published on 2006 Elsevier B.V.

Australian Patent Office, Office Action in Australian Patent Application No. 2009238317, dated Apr. 14, 2011.
Russian Patent Office, Office Action in Russian Patent Application No. 2009142016, dated Jan. 25, 2011.
Bull, S., "Surface Engineering of Ceramics", Materials World, vol. 1 No. 6, pp. 340-342, Jun. 1993.
Japanese Patent Office, Office Action in Japanese Patent Application No. 2009260208, dated Mar. 13, 2012.
Bull, S., "Surface Treatment for Ceramics", http://www.azom.com/details.asp?ArticleID=746, obtained May 9, 2008, source: Materials World, vol. 1, No. 6, pp. 340-342, Jun. 1993.
European Patent Office, Partial European Search Report in European Patent Application No. EP09252586, dated Apr. 25, 2012.

* cited by examiner

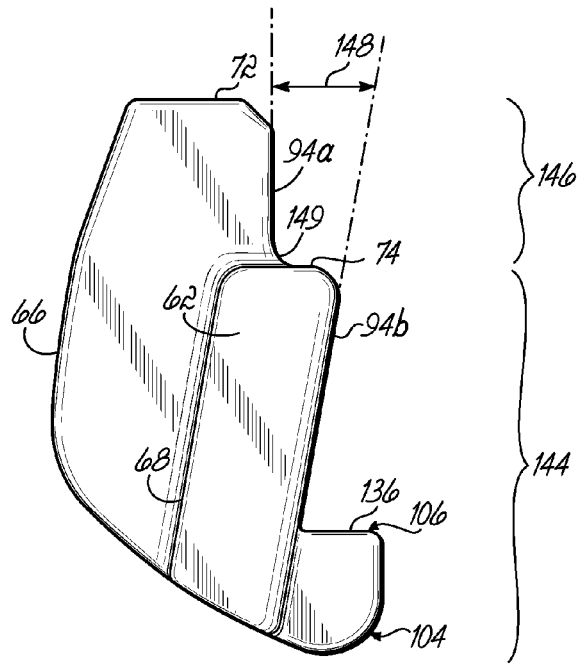
FIG. 9
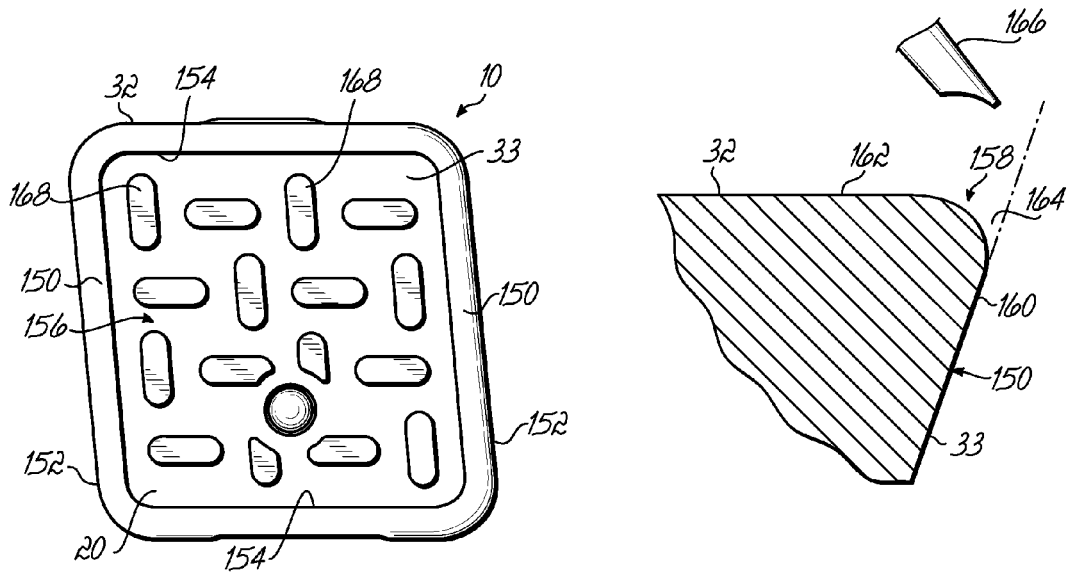
FIG. 10
FIG. 11

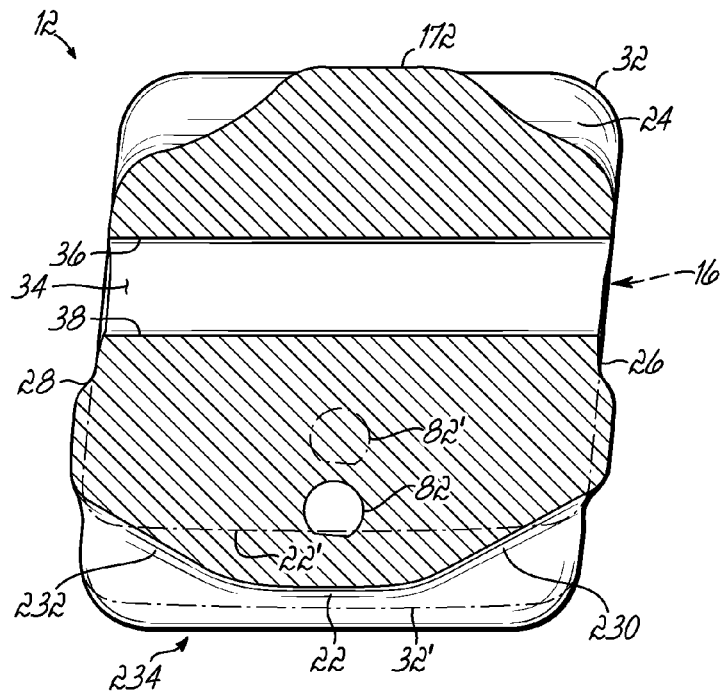
FIG. 18
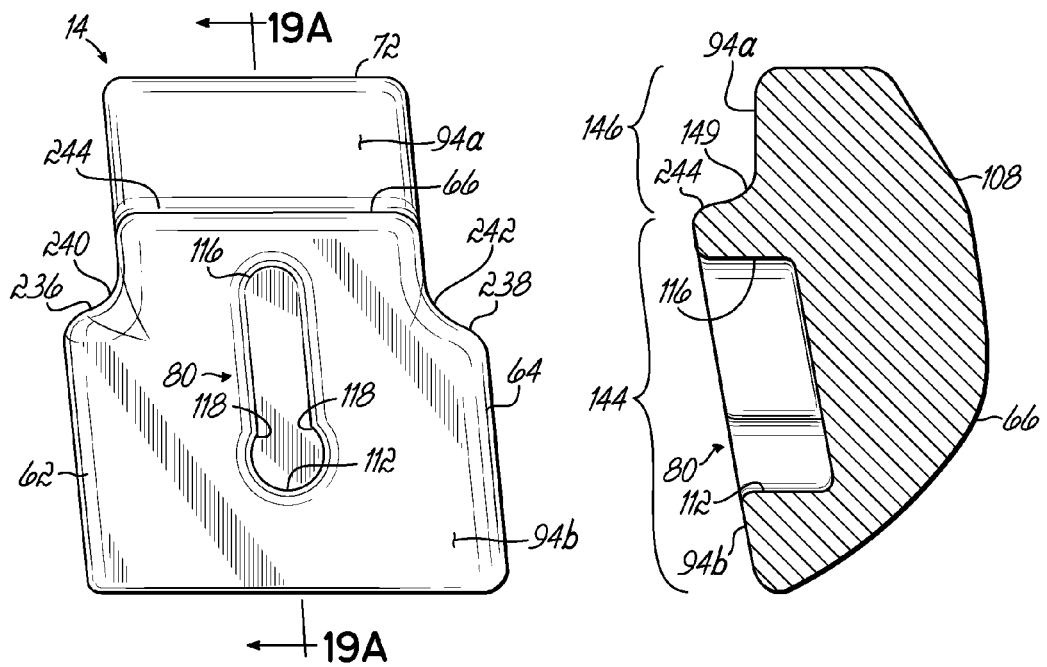
FIG. 19
FIG. 19A

AESTHETIC ORTHODONTIC BRACKET AND METHOD OF MAKING SAME

CROSS REFERENCE TO RELATED CASES

This application claims the benefit of U.S. Provisional Patent Application Ser. No. 61/088,519 filed Aug. 13, 2008, and the benefit of U.S. Provisional Patent Application Ser. No. 61/106,358 filed Oct. 17, 2008; the disclosures of which are incorporated by reference herein in their entirety.

TECHNICAL FIELD

The invention relates generally to orthodontic brackets and, more particularly, to aesthetic orthodontic brackets having movable closure members such as slides or latches.

BACKGROUND

Orthodontic brackets represent a principal component of corrective orthodontic treatments devoted to improving a patient's occlusion. In conventional orthodontic treatments, an orthodontist or an assistant affixes brackets to the patient's teeth and engages an archwire into a slot of each bracket. The archwire applies corrective forces that coerce the teeth to move into orthodontically correct positions. Traditional ligatures, such as small elastomeric O-rings or fine metal wires, are employed to retain the archwire within each bracket slot. Due to difficulties encountered in applying an individual ligature to each bracket, self-ligating orthodontic brackets have been developed that eliminate the need for ligatures by relying on a movable latch or slide for captivating the archwire within the bracket slot.

Conventional orthodontic brackets are ordinarily formed from stainless steel, which is strong, nonabsorbent, weldable, and relatively easy to form and machine. Patients undergoing orthodontic treatment using metal orthodontic brackets, however, may be embarrassed by the visibility of metal, which is not cosmetically pleasing. To improve the cosmetic appearance, certain conventional orthodontic brackets incorporate a bracket body of a transparent or translucent non-metallic material, such as a polymer resin or a ceramic, that assumes or mimics the color or shade of the underlying tooth. Such orthodontic brackets may rely on a metallic insert lining the archwire slot for strengthening and reinforcing the bracket body in the vicinity of the archwire slot. As a result, the appearance of metal in the patient's mouth, while still present to some degree, is less noticeable in ordinary view and, therefore, brackets characterized by a non-metallic bracket body are more aesthetically pleasing. Forming bracket bodies from transparent/translucent material, for example ceramic materials, has become desirable due to the improved aesthetics. However, ceramic materials are brittle and subject to a greater likelihood of fracture in use. Consequently, there is a need for ceramic brackets that are resistant to pressures needed to move teeth to their orthodontically correct positions.

While forming traditional, non self-ligating bracket bodies from transparent or translucent materials has generally improved the aesthetics of these brackets, improved aesthetics for self-ligating brackets has heretofore remained problematic. By way of example, current aesthetic self-ligating orthodontic brackets may use a transparent or translucent bracket body, but continue to utilize a closure member (e.g., ligating slide) made out of metal. One such example of this arrangement is disclosed in U.S. Patent Publication No. 2004/0072117, the disclosure of which is incorporated by reference herein in its entirety. These metal closure members may visibly detract from the aesthetic appearance desired by most patients, especially for the brackets attached to incisors and canines located in the anterior of the oral cavity. These self-ligating brackets have maintained the use of metal closure members generally because of the strength, ductility, and toughness required of such members. Thus, the aesthetics of self-ligating brackets has yet to be fully realized.

Consequently, there is a need for an improved, more fully aesthetic self-ligating orthodontic bracket that overcomes this and other deficiencies of conventional self-ligating orthodontic brackets.

SUMMARY OF INVENTION

To these ends, an orthodontic bracket for coupling an archwire with a tooth comprises a bracket body configured to be mounted to the tooth. The bracket body includes an archwire slot adapted to receive the archwire therein and a movable member engaged with the bracket body. The movable member is movable relative to the body between an opened position in which the archwire is insertable into the archwire slot and a closed position in which the movable member retains the archwire in the archwire slot. The bracket body and the movable member are made from a transparent or translucent ceramic material.

In one embodiment, the orthodontic bracket comprises a retention mechanism for limiting the movement of the movable member toward the open position, and a first stop feature that is separate from the retention mechanism for limiting movement of the movable member toward the closed position. The retention mechanism includes an apparent contact area between the retention mechanism and one of the movable member and bracket body. The first stop feature includes a first contact area between the movable member and bracket body that is greater than the apparent contact area.

In one embodiment, the bracket body includes a support surface that at least in part defines a slide engagement track. The movable member engages with the slide engagement track. At least a portion of the support surface is positioned lingually of a labial edge of the archwire slot.

In one embodiment, the bracket body comprises a polycrystalline ceramic having a grain size distribution characterized by an average grain size in the range of larger than 3.4 µm to about 6 µm. In one embodiment, the orthodontic bracket further comprises a ligating slide comprising the polycrystalline ceramic.

In yet another embodiment, an orthodontic bracket comprises a bracket body configured to be mounted to the tooth, including an archwire slot configured to receive the archwire therein, the bracket body comprising a polycrystalline ceramic having a grain size distribution characterized by an average grain size in the range of about 3.5 µm to about 5 µm, by having up to about 50% of the grains being less than about 3 µm in size, by having up to about 90% of the grains being less than about 10 µm in size, and by having grains larger than 10 µm in size occupying up to about 50% of the volume of the bracket body. The polycrystalline ceramic has a fracture toughness of at least $4.0 \text{ MPa·m}^{1/2}$.

In still another embodiment of the present invention, a method of making an orthodontic bracket comprises molding a bracket body from a ceramic powder and sintering the molded body to form a sintered body having a grain size distribution characterized by an average grain size in the range of larger than 3.4 µm to about 6 µm.

BRIEF DESCRIPTION OF THE DRAWINGS

The accompanying drawings, which are incorporated in and constitute a part of this specification, illustrate embodi

FIG. 9 is a side elevation view of the ligating slide shown in FIG. 1;

FIG. 10 is a rear elevation view of the self-ligating orthodontic bracket shown in FIG. 1;

FIG. 11 is an enlarged view of encircled portion 11 shown in FIG. 6;

FIG. 18 is a cross-sectional view of the self-ligating orthodontic bracket shown in FIG. 16 taken generally along line 18-18;

FIG. 19 is a rear elevation view of the ligating slide shown in FIGS. 16 and 17;

FIG. 19A is a cross-sectional view of the ligating slide shown in FIG. 19 taken along line 19A-19A;

DETAILED DESCRIPTION

Although the invention will be described next in connection with certain embodiments, the invention is not limited to practice in any one specific type of orthodontic bracket. The description of the embodiments of the invention is intended to cover all alternatives, modifications, and equivalent arrangements as may be included within the spirit and scope of the invention as defined by the appended claims. In particular, those skilled in the art will recognize that the components of the embodiments of the invention described herein could be arranged in multiple different ways.

Figure 1:
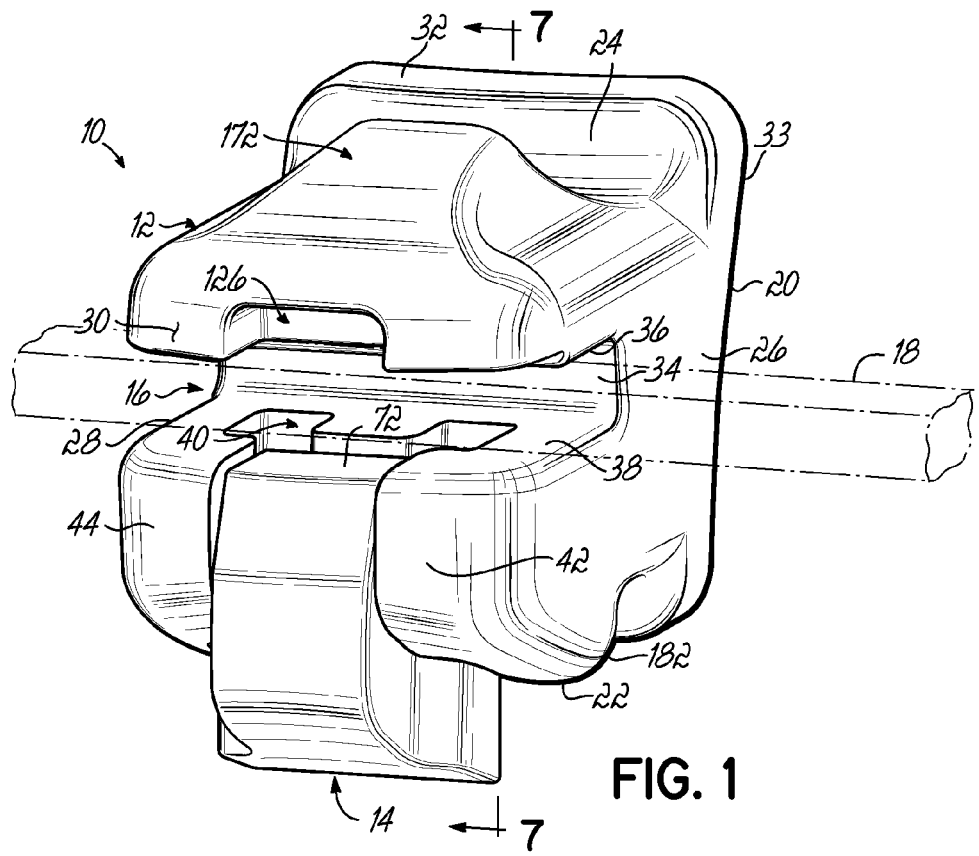
- FIG. 1 is a perspective view of a self-ligating orthodontic bracket in accordance with one embodiment of the invention with a ligating slide shown in an opened position.
Figure 2:
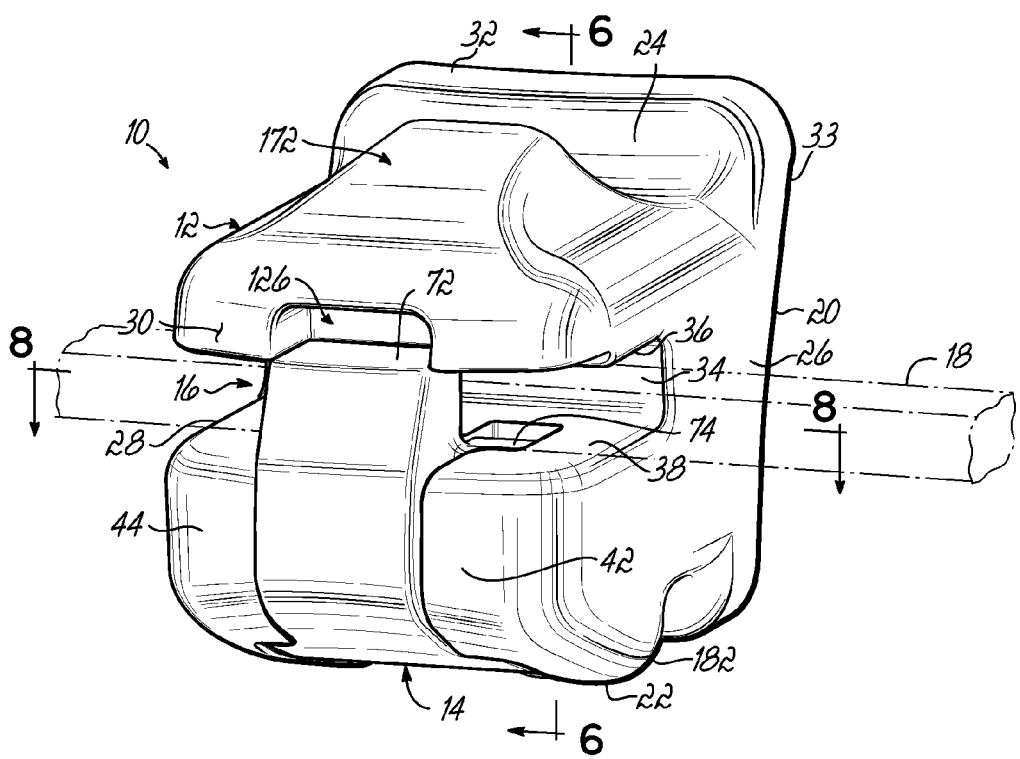
FIG. 2 is a perspective view of the self-ligating orthodontic bracket shown in FIG. 1 with the ligating slide shown in a closed position.

Referring now to the drawings, and to FIGS. 1 and 2 in particular, an orthodontic bracket 10 includes a bracket body 12 and a movable closure member coupled to the bracket body 12. In one embodiment, the movable closure member may include a ligating slide 14 slidably coupled with the bracket body 12. The bracket body 12 includes an archwire slot 16 formed therein adapted to receive an archwire 18 (shown in phantom) for applying corrective forces to the teeth. The ligating slide 14 is movable between an opened position (FIG. 1) in which the archwire 18 is insertable into the archwire slot 16, and a closed position (FIG. 2) in which the archwire 18 is retained within the archwire slot 16. The bracket body 12 and ligating slide 14 collectively form a self-ligating orthodontic bracket 10 for use in corrective orthodontic treatments. Moreover, while the movable closure member is described herein as a ligating slide, the invention is not so limited as the movable closure member may include other movable structures (e.g., latch, spring clip, door, etc.) that are capable of moving in any appropriate manner between an opened and closed position.

The orthodontic bracket 10, unless otherwise indicated, is described herein using a reference frame with the bracket 10 attached to a labial surface of a tooth on the upper jaw. Consequently, as used herein, terms such as labial, lingual, mesial, distal, occlusal, and gingival used to describe bracket 10 are relative to the chosen reference frame. The embodiments of the invention, however, are not limited to the chosen reference frame and descriptive terms, as the orthodontic bracket 10 may be used on other teeth and in other orientations within the oral cavity. For example, the bracket 10 may also be coupled to the lingual surface of the tooth or be located on the lower jaw and be within the scope of the invention.

Those of ordinary skill in the art will recognize that the descriptive terms used herein may not directly apply when there is a change in reference frame. Nevertheless, the invention is intended to be independent of location and orientation within the oral cavity and the relative terms used to describe embodiments of the orthodontic bracket are to merely provide a clear description of the examples in the drawings. As such, the relative terms labial, lingual, mesial, distal, occlusal, and gingival are in no way limiting the invention to a particular location or orientation.

When mounted to the labial surface of a tooth carried on the patient's upper jaw, the bracket body 12 has a lingual side 20, an occlusal side 22, a gingival side 24, a mesial side, 26, a distal side 28 and a labial side 30. The lingual side 20 of the bracket body 12 is configured to be secured to the tooth in any conventional manner, such as for example, by an appropriate orthodontic cement or adhesive or by a band around an adjacent tooth (not shown). The lingual side 20 may further be provided with a pad 32 that defines a bonding base 33 adapted to be secured to the surface of the tooth. The pad 32 may be coupled to the bracket body 12 as a separate piece or element, or alternatively, the pad 32 may be integrally formed with the bracket body 12. The bracket body 12 includes a base surface 34 and a pair of opposed slot surfaces 36, 38 projecting labially from the base surface 34 that collectively define the archwire slot 16 extending in a mesial-distal direction from mesial side 26 to distal side 28. The slot surfaces 36, 38 and base surface 34 are substantially encapsulated or embedded within the material of the bracket body 12. The archwire slot 16 of the bracket body 12 may be designed to receive the orthodontic archwire 18 in any suitable manner.

Figure 4:
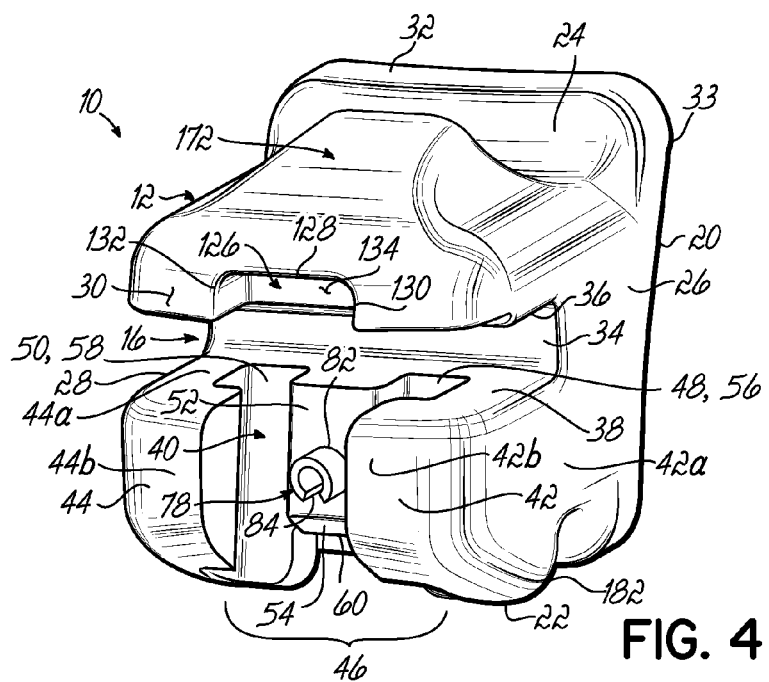
FIG. 4 is a perspective view of the self-ligating orthodontic bracket shown in FIG. 1 with the slide removed.

In reference to FIG. 4, the bracket body 12 further includes a support surface 40 extending in a generally gingival-occlusal direction from slot surface 38. A pair of opposed guides 42, 44 are carried by support surface 40 and are positioned on respective mesial and distal sides 26, 28 thereof. The guides 42, 44 are generally L-shaped and each includes a first leg 42a, 44a projecting from support surface 40 in the labial direction. Guide 42 has a second leg 42b or ear projecting in the distal direction while guide 44 has a second leg 44b or ear projecting in the mesial direction so that collectively guides 42, 44 partially overlie support surface 40. Support surface 40 and guides 42, 44 collectively define a slide engagement track 46 for supporting and guiding ligating slide 14 within bracket body 12.

The support surface 40 includes a mesial portion 48, a distal portion 50, and a central portion 52 intermediate the mesial and distal portions 48, 50. Guides 42, 44 are configured to overlie, but be spaced from, mesial and distal portions 48, 50, respectively, so as to receive the ligating slide 14. The central portion 52 includes a raised boss 54 that projects generally in the labial direction, the purpose of which is discussed in more detail below. Such a configuration essentially defines gingivally-occlusally directed tracks or grooves 56, 58 in the support surface 40. In addition, the central portion 52 of support surface 40 includes a recess or cutout 60 at an occlusal end thereof that defines a stop surface. As explained in more detail below, the stop surface is configured to cooperate with the ligating slide 14 to accommodate imposed forces (e.g., mastication forces) on the bracket 10 in an improved manner.

As noted above, to improve the aesthetics of the orthodontic bracket 10, the bracket body 12 is formed from a translucent or transparent non-metallic material. For example, the bracket body 12 may be formed from a transparent or translucent ceramic material. Additionally, the bracket body 12 may be tooth colored. In one embodiment, the ceramic material may be a polycrystalline alumina or aluminum oxide. However, by way of example and not limitation, other polycrystalline ceramic materials may be used, such as polycrystalline zirconia or zirconium oxide. Accordingly, in one embodiment, the bracket body 12 may be formed by ceramic injection molding (CIM) followed by sintering and/or hot isostatic pressing (HIPing).

In yet another embodiment, a portion of the bracket body 12 or the entire surface thereof may be treated to increase the torque strength of the bracket body 12. By way of example, the bracket body 12 may have a coating deposited or otherwise formed thereon. For example, the coating may be deposited by physical vapor deposition (PVD) or chemical vapor deposition (CVD) with a thickness of up to about 15 μm. Further, the coating may be amorphous, nanocrystalline, or have a microstructure that contains grains that are finer than the grains of the bracket body 12. In one embodiment, rather than grinding and/or polishing the surface, a portion or all of the surfaces of the bracket body 12 may be ion milled or acid etched to remove surface imperfections and generate compressive surface stresses therein, thereby strengthening the bracket body 12. In addition, or alternatively, the surfaces may be metal ion bombarded, mixed metal ion bombarded, or laser melted to improve fracture toughness. It will be appreciated that a combination of one or more surface treatments may be utilized to increase the torque strength of the bracket body 12.

Figure 3:
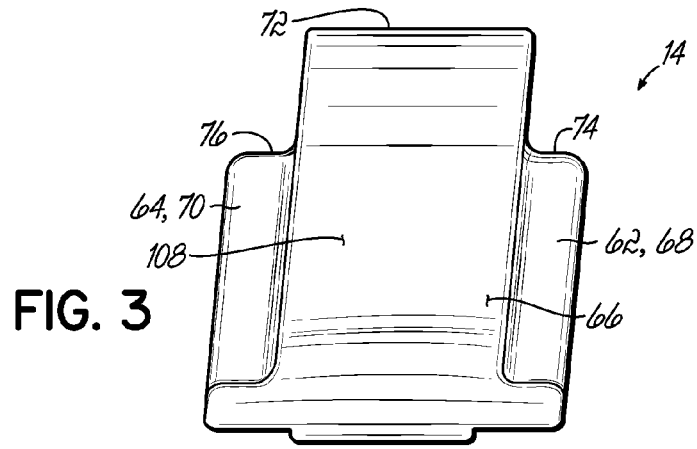
FIG. 3 is a front elevation view of the ligating slide shown in FIG. 1.

As shown in FIG. 3, the ligating slide 14 includes a mesial portion 62, a distal portion 64, and a central portion 66 intermediate the mesial and distal portions 62, 64. Guides 42, 44 are configured to overlie mesial and distal portions 62, 64, respectively, and central portion 66 may be configured such that the labial side of central portion 66 is substantially flush with the labial side of the guides 42, 44 (FIG. 2). Such a configuration essentially defines gingivally-occlusally directed tracks or grooves 68, 70 in the labial side of the ligating slide 14 which move along guides 42, 44 as the ligating slide 14 is moved between the opened and closed positions. The mesial and distal portions 62, 64 do not extend the full gingival-occlusal extent of the ligating slide 14, but instead stop short of the gingival side 72 to define two, generally planar platform surfaces 74, 76, respectively. As shown in FIG. 2, and discussed in more detail below, when the ligating slide 14 is in the closed position, the platform surfaces 74, 76 may be adjacent or form a portion of the archwire slot 16, and more particularly, form a portion of the slot surface 38 that bounds a side of archwire 18.

In contrast to many aesthetic self-ligating brackets, the ligating slide 14 may also be formed from a translucent or transparent material. For example, the ligating slide 14 may be formed from a transparent or translucent ceramic material. In one embodiment, the ceramic material may be the same as that used to form the bracket body 12. Those of ordinary skill in the art will recognize, however, that there are other suitable materials which would provide an aesthetic ligating slide 14. In addition, to improve the strength and aesthetics, the ligating slide 14 may be surface treated in a manner similar to that described above for bracket body 12. Advantageously, forming both the bracket body 12 and ligating slide 14 from a transparent or translucent material will reduce the visibility of the orthodontic bracket when it is secured to a patient's tooth.

Figure 5:
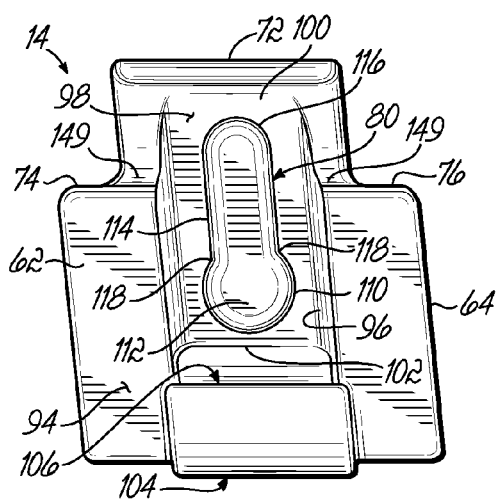
FIG. 5 is a rear elevation view of the ligating slide shown in FIG. 1.

As shown in FIGS. 4 and 5, the orthodontic bracket 10 includes a securing mechanism that secures the ligating slide 14 in at least the closed position. To this end, the securing mechanism includes a projecting portion in one of the bracket body 12 or ligating slide 14 and a receiving portion in the other of the bracket body 12 or ligating slide 14 that cooperate to keep the ligating slide 14 in at least the closed position. The securing mechanism may further prevent the ligating slide 14 from detaching from the bracket body 12. In one exemplary embodiment, the securing mechanism includes a resilient engagement member, such as a generally elongate, cylindrical, tubular spring pin 78 (FIG. 4), coupled to the bracket body 12, and a retaining slot 80 (FIG. 5) formed in the ligating slide 14. Although this embodiment is described with the spring pin 78 associated with the bracket body 12 and the retaining slot 80 associated with the ligating slide 14, those of ordinary skill in the art will recognize that the invention is not so limited. For example, a spring pin may be coupled to the ligating slide and a suitable retaining slot may be formed in the bracket body.

Figure 6:
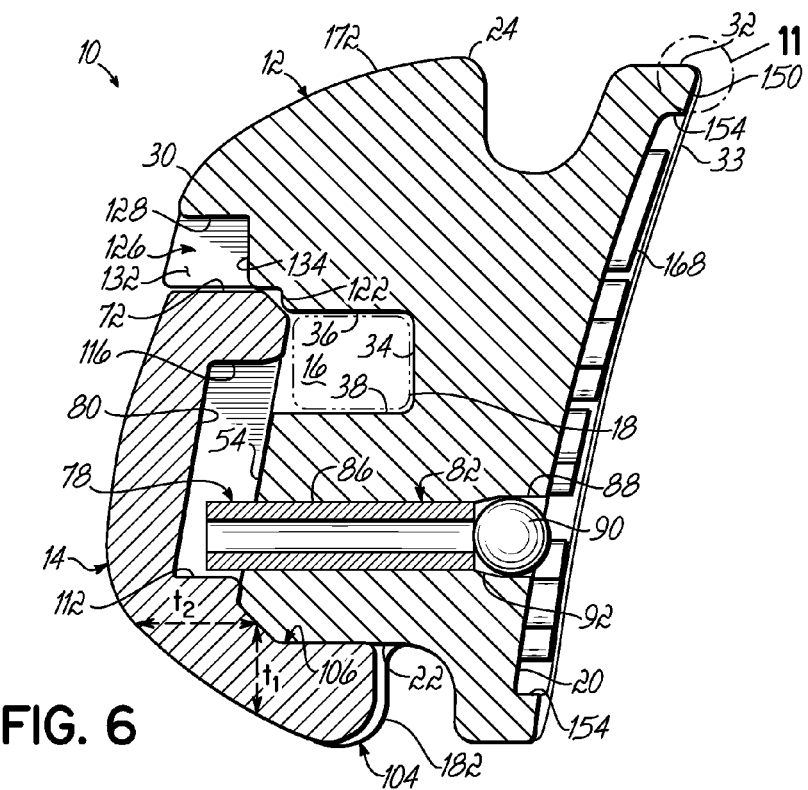
FIG. 6 is a cross-sectional view of the self-ligating orthodontic bracket shown in FIG. 2 taken generally along line 6-6.
Figure 7:
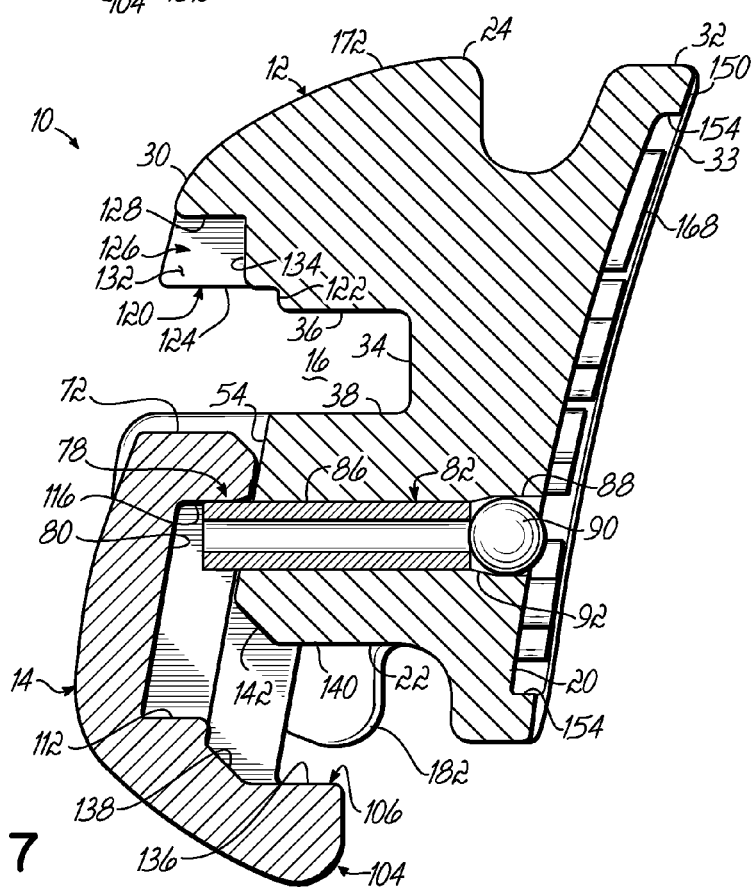
FIG. 7 is a cross-sectional view of the self-ligating orthodontic bracket shown in FIG. 1 taken generally along line 7-7.

As shown in FIGS. 4, 6, and 7, spring pin 78 includes a first portion and a second portion. The first portion of spring pin 78 is configured to be received within a bore 82 formed in support surface 40. The second portion of spring pin 78 projects away from support surface 40 in a general labial direction so as to extend into slide engagement track 46. The spring pin 78 includes a cutout or slit 84, the purpose of which is described below, formed in the sidewall thereof and extends along at least a portion of the length of the spring pin 78. The spring pin 78 may be formed, for example, through a rolling process so as to define the slit 84, or alternatively, may be formed by cutting a tubular member to form slit 84. Additionally, the spring pin 78 may be formed from materials including stainless steel, titanium alloys, NiTi-type superelastic materials, or other suitable materials.

The bore 82 is positioned occlusally of the archwire slot 16 and extends from the lingual side 20 to the support surface 40 of bracket body 12. Additionally, the bore 82 may be formed in the raised boss 54 of central portion 52. Locating spring pin 78 within raised boss 54 provides additional support to spring pin 78 and prevents or reduces cantilevered bending or flexing of spring pin 78. The bore 82 includes a first portion 86 open to support surface 40 and adapted to receive the spring pin 78 therein, and a second portion 88 open at the lingual side 20 of bracket body 12 and adapted to receive an occluding member configured to secure the spring pin 78 within bore 82. In one embodiment, the occluding member may be a ball 90. The occluding member, however, is not so limited, as other occluding members may also be used to secure spring pin 78 within bore 82. A generally tapered transition region 92 may be disposed between the first and second bore portions 86, 88.

During assembly, the spring pin 78 is inserted into the bore 82 from the lingual side 20 (and with the ligating slide 14 engaged with bracket body 12) so as to be positioned within first bore portion 86. The ball 90 is inserted into the second bore portion 88 and secured to the bore 82. By way of example, the ball 90 may be adhesively coupled with bore 82. Those of ordinary skill in the art may recognize other ways to secure the ball 90 within bore 82. The cross dimension of second bore portion 88 may be greater than a cross dimension of the first bore portion so as to facilitate insertion of the spring pin 78 within bore 82. In particular, the tapered transition region 92 may facilitate insertion of the spring pin 78 within bore 82 during the assembly process. In one embodiment, ball 90 may be formed of zirconia, but other suitable materials, such as PMMA, polycarbonate, glass, and the like, may also be used to form ball 90. Although the spring pin 78 may be formed from metal, the spring pin 78 (and ball 90 should it be made from a non-aesthetic material) is positioned relatively deep within the orthodontic bracket 10 to minimize any impact on the aesthetics of the bracket 10.

As shown in FIG. 5, the lingual side 94 of ligating slide 14 includes a cavity 96 having a base surface 98, a gingival end 100, and an occlusal end 102. The gingival end 100 is open so as to receive the raised boss 54 therein as the ligating slide 14 is moved between the opened and closed positions. The occlusal end 102 of cavity 96 is closed off by a tab member 104 extending outwardly (e.g., lingually) from lingual side 94 and having a contacting surface 106 confronting the cavity 96, the purpose of which is discussed in more detail below.

The retaining slot 80 is formed in the base surface 98 of the cavity 96 and extends generally in the gingival-occlusal direction (e.g., in the direction of movement of ligating slide 14). The retaining slot 80 may be formed so as to extend completely through the slide 14 in the labial-lingual direction (not shown), or so as to extend only partially through the slide 14, and therefore not be visible from a labial side 108 of the slide 14 (e.g., a blind slot), as shown in FIGS. 3 and 5. Such a blind slot configuration reduces the sites on the labial side of the bracket 10 where food or other material from the oral cavity could collect, thereby improving overall hygiene. In one embodiment, the retaining slot 80 has an enlarged portion 110 at an occlusal end 112 of the slot 80 in communication with a straight segment portion 114 having a closed gingival end 116. The enlarged portion 110 may be circular, as shown, or have other suitable shapes. The cross dimension of the circular portion 110 is larger than the cross dimension of the straight segment portion 114 to define a pair of opposed protrusions 118 at the transition therebetween.

When the ligating slide 14 is coupled to the bracket body 12, the spring pin 78 is received in retaining slot 80, which moves relative to the spring pin 78 as the ligating slide 14 is moved between the opened and closed positions. The spring pin/retaining slot configuration provides for securing the ligating slide 14 in at least the closed position. To this end, the slit 84 in the spring pin 78 allows the spring pin 78 to be generally radially flexed or elastically deformed. Thus, the spring pin 78 is capable of radially expanding and contracting depending on the radial force being imposed thereon. To this end, the slit 84 in the spring pin 78 allows at least the slit portion to be generally radially flexed or elastically deformed relative to its central axis 69. As used herein, radially flexed includes not only uniform radial changes, but also includes non-uniform or partial radial changes, such as that which occurs during squeezing of a resilient C clip. In other words, at least a portion of spring pin 78 has a first effective diameter or radius of curvature (such as in an unbiased state) but is capable of being flexed, such as by squeezing the spring pin 78, so as to have a second effective diameter or radius of curvature smaller than the first effective diameter or radius of curvature. While the slit 84 in spring pin 78 allows for radial contraction/expansion, such movement may be achieved in other ways.

In operation, when the ligating slide 14 is in the closed position (FIG. 2), the spring pin 78 is disposed in the enlarged portion 110 of retaining slot 80 and is permitted to radially expand such that the spring pin 78 engages the wall of enlarged portion 110. Those of ordinary skill in the art will recognize that the spring pin 78 does not have to engage the wall of enlarged portion 110, but must at least have a cross dimension (e.g., diameter) when radially expanded that is larger than the cross dimension of the straight segment portion 114. When so disposed in the enlarged portion 110, the protrusions 118 provide a threshold level of resistance to any movement of the ligating slide 14 away from the closed position and toward the opened position. However, if a sufficiently large opening force is applied to the ligating slide 14 in the occlusal direction, for example, the interaction between the retaining slot 80 and spring pin 78 causes the pin 78 to radially contract (due to the squeezing imposed by the slot 80)

so that the spring pin 78 moves past the protrusions 118 and into the straight segment portion 114 of the retaining slot 80.

Once positioned in the straight segment portion 114, the spring pin 78 bears against the sides thereof such that a threshold sliding force, which is less than, and perhaps significantly less than the opening force, must be imposed to overcome the drag and move the ligating slide 14 relative to the bracket body 12 as spring pin 78 traverses straight segment portion 114. Thus, once opened, the ligating slide 14 does not just freely slide or drop to the fully opened position, but must be purposefully moved toward the opened position. If the ligating slide 14 is only partially opened, the slide 14 may be configured to maintain its position relative to the bracket body 12 (due to, for example, the friction forces between the spring pin 78 and the slide 14) until the threshold sliding force is imposed to continue moving the slide 14 toward the opened position. Such a configuration reduces the likelihood of unintentionally closing the slide 14 during, for example, an orthodontic treatment. When the ligating slide 14 is moved toward the closed position, the spring pin 78 recovers or snaps back to its radially expanded position as the spring pin 78 enters the enlarged portion 110 to once again secure the ligating slide 14 in the closed position.

As introduced above, the raised boss 54 supports the spring pin 78 during the opening and closing of the ligating slide 14. In this regard, when the ligating slide 14 is moved toward the open position, any drag forces from contact of the spring pin 78 with the retaining slot 80 may create a shear-type force on the pin 78. The raised boss 54 reduces the likelihood that the pin 78 will plastically deform or fracture when the ligating slide 14 moves past the pin 78 because it supports the length of the pin 78 that extends from the surface 40. By contrast, without the raised boss 54, and where a length of the pin 78 projects labially from the support surface 40, it is more likely that the pin 78 would experience a cantilever-type or torque force sufficient to bend or break the pin 78 about the edge of the bore 82 when the slide 14 moves in either direction.

The securing mechanism, including spring pin 78 and retaining slot 80, is more fully disclosed in pending U.S. patent application Ser. No. 12/147,877 (the '877 application), the disclosure of which is incorporated by reference herein in its entirety. Additionally, the other securing mechanisms disclosed in the '877 application may also be used for the aesthetic orthodontic bracket 10 as disclosed herein. Thus, the securing mechanism is not limited to the spring pin/retaining slot configuration shown in the figures and described above.

In addition to sufficiently securing the ligating slide 14 in at least the closed position, the securing mechanism may also operate as a retention mechanism to prevent or reduce accidental or unintentional detachment of the ligating slide 14 from the bracket body 12 during use, such as when the ligating slide 14 is in the opened position. To this end, the length of the retaining slot 80 may limit the gingival-occlusal travel of ligating slide 14 relative to the bracket body 12. For example, the spring pin 78 may abut the gingival end 116 of the retaining slot 80 when the ligating slide 14 is in the fully opened position. Because the gingival end 116 closes the retaining slot 80, further movement of the ligating slide 14 in an occlusal direction relative to bracket body 12 is prohibited, and ligating slide 14 cannot become separated or detached from bracket body 12.

Similarly, in the fully closed position of the ligating slide 14, the spring pin 78 is positioned in the enlarged portion 110 at the occlusal end 112 of the retaining slot 80, which may prohibit further movement of the ligating slide 14 in the gingival direction relative to the bracket body 12. As discussed in more detail below, the orthodontic bracket 10 may include other features that, in lieu of or in addition to the securing mechanism, prevent movement of the ligating slide 14 in the gingival direction relative to the bracket body 12.

In this regard, designs that limit or stop gingival movement of the ligating slide 14 relative to bracket body 12 using only the spring pin 78 may be susceptible to premature failure of the securing mechanism. In these designs, all the forces that are imposed on the ligating slide 14, such as during chewing, are transmitted to the bracket body 12 via the spring pin 78. Due to the relatively small contact area between the spring pin 78 and ligating slide 14, the forces transmitted to the bracket body 12 through spring pin 78 may be sufficient to shear, notch, or otherwise damage the spring pin 78. Thus, as is described more fully below, it may be desirable to limit the gingival movement of the ligating slide 14 using stop surfaces with increased areas of contact between the ligating slide 14 and bracket body 12. The increased contact area will essentially spread the imposed loads on the ligating slide 14 across a greater area of the bracket body 12. Such a configuration will prevent or reduce the risks of premature failure of the securing mechanism. In this regard, the stop surfaces may reduce or prevent the spring pin 78 from bottoming out on the occlusal end 112 of the retaining slot 80. Additionally, when the ligating slide 14 is in the closed position, the stop surfaces define contact areas that are greater than an apparent contact area between the spring pin 78 and retaining slot 80 in the absence of the stop surfaces.

To this end, when the ligating slide 14 is in the closed position, the gingival side 72 of the ligating slide 14 may be configured to engage a first contacting or stop surface of the bracket body 12. In this regard, as shown in FIGS. 6 and 7, the orthodontic bracket 10 may include an overshoot feature configured as a cutout 120 formed in the labial side 30 of the bracket body 12 adjacent slot surface 36. The cutout 120 defines a ledge 122 which extends above slot surface 36 and is configured to engage or be adjacent the lingual side 94 of ligating slide 14 when the slide 14 is in the closed position. Providing such on overshoot eases the acceptable tolerances in the coupling of the ligating slide 14 and bracket body 12 so as to cover the archwire slot 16 when in the closed position.

Cutout 120 also defines a gingival wall 124 that overhangs the gingival side 72 of the ligating slide 14 when in the closed position, as shown in FIG. 6. This overhang prevents or reduces food or other material in the oral cavity from contacting the gingival side 72 of the slide 14 and inadvertently moving the slide 14 toward the opened position. The gingival wall 124 of cutout 120 may also provide the first contacting surface. In this regard, when the ligating slide 14 is in the closed position, the gingival side 72 of the slide 14 may be configured to engage the gingival wall 124 of the cutout 120 prior to the spring pin 78 bottoming out on the occlusal end 112 of retaining slot 80. The contact between the gingival side 72 of the ligating slide 14 and gingival wall 124 of bracket body 12 increases the area over which forces imposed on the ligating slide 14 are transmitted to the bracket body 12. Furthermore, when the ligating slide 14 is in the closed position, a portion of the retaining slot 80 may be exposed to the archwire slot 16, as shown in FIG. 6.

As shown in the figures, orthodontic bracket 10 may include a tool receptacle 126 that cooperates with a tool (not shown) for moving the ligating slide 14 away from the closed position and toward the opened position. With reference to FIGS. 4, 6 and 7, the labial side 30 of bracket body 12 includes tool receptacle 126 defining a gingival wall 128, a mesial wall 130, a distal wall 132, and a labial wall 134. The receptacle 126, however, is open along an occlusal end thereof so as to be accessible to at least a portion of ligating slide 14. For example, the tool receptacle 126 may be open to the gingival side 72 of ligating slide 14. Various tools and methods for using tool receptacle 126 are more fully disclosed in U.S. patent application Ser. No. 12/147,854, the disclosure of which is incorporated by reference herein in its entirety. As illustrated in these figures, the intersection of the tool receptacle 126 and cutout 120 diminishes the area of the first contacting surface between the gingival side 72 of ligating slide 14 and the gingival wall 124 of cutout 120. For example, with tool receptacle 126 formed in bracket body 12, the first contacting surface may be strips along the occlusal edges of mesial, distal, and labial walls 130, 132, and 134, respectively.

Orthodontic bracket 10 may further include a second contacting or stop surface between the ligating slide 14 and bracket body 12 that limits or stops gingival movement of the ligating slide 14 relative to bracket body 12. The second contacting surface may operate alone or in conjunction with the first contacting surface as described above. In this regard, and as shown in FIGS. 6 and 7, when the ligating slide 14 is in the closed position, the contacting surface 106 of tab member 104 may be configured to engage bracket body 12 prior to the spring pin 78 bottoming out on the occlusal end 112 of retaining slot 80. More particularly, the occlusal side 22 of bracket body 12 may provide the second contacting surface. To this end, the contacting surface 106 of tab member 104 includes a first engaging portion 136 and a second engaging portion 138 that respectively engage a first engaging portion 140 and second engaging portion 142 of bracket body 12. The contact between the tab member 104 of the ligating slide 14 and bracket body 12 increases the area over which forces imposed on the ligating slide 14 are transmitted to the bracket body 12. Thus, the likelihood of premature failure of the securing mechanism may be reduced.

The relationship between the tab member 104 and bracket body 12 may have additional benefits. For example, when the ligating slide 14 is in the closed position, the tab member 104 is positioned in recess 60 in support surface 40 and at least partially fills a void between the guide members 42, 44 adjacent the occlusal side 22 of bracket body 12. Filling such a void with the tab member 104 reduces the sites available for plaque and/or food buildup. Moreover, as shown in FIGS. 6 and 7, the second engaging portions 138, 142 may be angled or chamfered relative to first engaging portions 136, 140. The chamfered configuration on the ligating slide 14 allows for an increased wall thickness in portions of slide 14. For example, as shown in FIG. 6, the thickness $t_1$ of the ligating slide 14 in a gingival-occlusal direction, and the thickness $t_2$ of the ligating slide 14 in the labial-lingual direction may be increased relative to more traditional non-chamfered configurations. The increased thicknesses provide additional strength and rigidity to the ligating slide 14.

In addition to the various features described above, orthodontic bracket 10 may include several other features that provide benefits to the design of the bracket and/or to the implementation of the bracket during orthodontic treatments. By way of example, one feature is directed to the position of the ligating slide 14 relative to the bracket body 12, and more particularly, relative to the archwire slot 16. In this regard, conventional self-ligating brackets typically have bracket bodies that form an archwire slot and bound the archwire on all but one side thereof. The unbounded side of the archwire slot is then closed off by the movable closure member. A substantial portion, if not all, of the closure member is generally positioned on the labial side of the archwire slot and as a result the bracket body must include structure extending labially of the archwire slot to accommodate the closure member, such as during movement between the opened and closed position. As a consequence, the labial-lingual width of the self-ligating orthodontic bracket is generally relatively large. The increased labial-lingual width not only makes the brackets more noticeable, and thus less aesthetically pleasing, but also may decrease comfort for the patient. Additionally, relatively large labial-lingual widths increase the occurrence of bond failure due to, for example, mastication forces.

Figure 8:
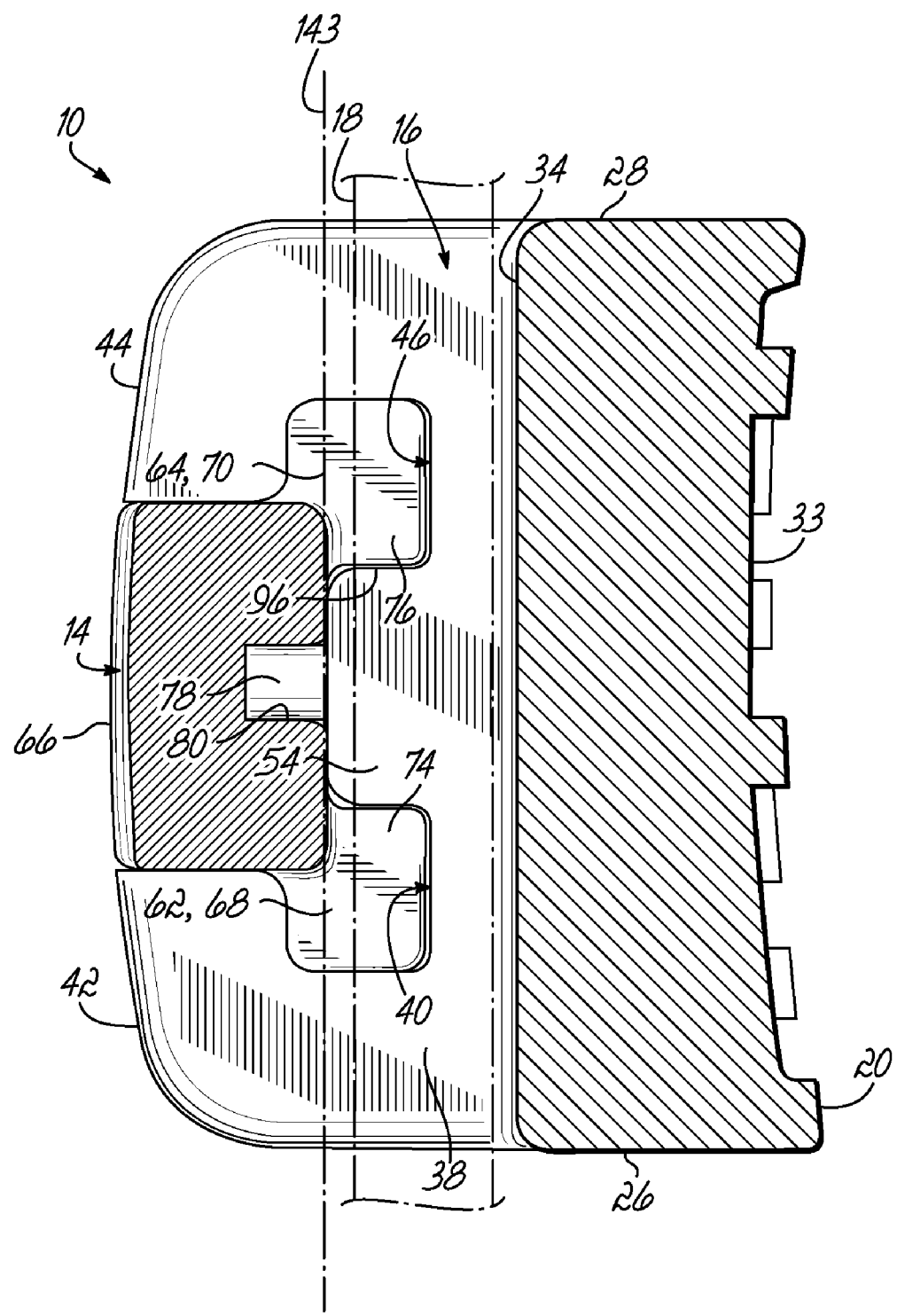
FIG. 8 is a cross-sectional view of the self-ligating orthodontic bracket shown in FIG. 2 taken generally along line 8-8.

To address such shortcomings of conventional self-ligating brackets, orthodontic bracket 10 is designed to provide a self-ligating feature with a decrease in the labial-lingual width, thus improving the aesthetics and comfort to the patient. In this regard, the ligating slide 14 has been moved lingually within the bracket body 12 relative to conventional self-ligating bracket designs. Thus, as shown in FIG. 8, the support surface 40 that defines slide engagement track 46 (FIG. 4) is no longer labial of the archwire slot 16, but includes a portion of which is now positioned lingual of a labial edge 143 of the archwire slot 16. In one embodiment, the slide engagement track 46 intersects the slot surface 38 at an intermediate location thereof, as shown in FIG. 8 (i.e., between base surface 34 and labial edge 143). Alternatively, however, the slide engagement track 46 may be partially closed off from the archwire slot 16 by an intervening wall (shown in FIG. 16 and described below) but still be positioned lingually of the labial edge 143 of archwire slot 16.

Moving the slide engagement track 46 lingually within the bracket body 12 results in a number of design features in ligating slide 14 to accommodate such movement. As illustrated in FIGS. 2 and 9, the ligating slide 14 includes a bracket-engaging portion 144 that confronts the bracket body 12, and a slot-covering portion 146 that confronts the archwire slot 16 when in the closed position. The transition between the two portions occurs adjacent the platform surfaces 74, 76. In reference to FIG. 9, in addition to stopping the mesial and distal portions 62, 64 short of the gingival side 72 to form platform surfaces 74, 76 (FIGS. 3 and 5), the lingual side 94a of the slot covering portion 146 is offset from the lingual side 94b of the bracket-engaging portion 144 in, for example, a generally labial direction. The offset, generally shown at 148, provides for movement of the ligating slide 14 along slide engagement track 46 that has been moved lingually within bracket body 12 and allows the slot-covering portion 146 to cover the archwire slot 16 so as not to interfere with the archwire 18, which it might otherwise do but for the offset 148. Furthermore, the corner 149 formed between the lingual side 94a of slot-covering portion 146 and platform surfaces 74, 76 is not sharp, but instead is curved or rounded so as to reduce the stress concentrations on the ligating slide 14 at the corner 149. By way of example, the corner 149 may have a radius of curvature of greater than approximately 0.003 inch.

In the particular embodiment shown, when in the closed position, the ligating slide 14 confronts and bounds the archwire 18 in the generally labial direction (e.g., one side of archwire 18 as shown in FIG. 6). Additionally, and as a result of the lingual movement of the ligating slide 14 within bracket body 12, the platform surfaces 74, 76 also confront the archwire 18 and may, for example, also bound the archwire by forming a portion of slot surface 38 (e.g., a second side of archwire 18 as shown in FIG. 8). In this regard, the platform surfaces 74, 76 may be configured to be flush with the slot surface 38 or may be slightly below (e.g., spaced occlusally of) slot surface 38. Locating the platform surfaces 74, 76 slightly below slot surface 38 may reduce the frictional engagement between the archwire 18 and archwire slot 16.

Moving the ligating slide 14 lingually within the bracket body 12 of orthodontic bracket 10 reduces the labial-lingual width of bracket 10. The reduced width in this direction improves the aesthetics by making the brackets less noticeable, improves the comfort of the brackets to the patient, and may further reduce the occurrence of bond failure.

In another aspect, functionality and use of orthodontic bracket 10 may be enhanced by the inclusion of additional features on the bonding base 33 of the pad 32. In this regard, there are several shortcomings of conventional brackets relative to the bonding process to the tooth. For example, it is not uncommon for excessive adhesive, used to bond the bracket to the tooth, to leak beyond the periphery of the bonding base of the bracket, thus requiring monitoring and cleanup. In some bracket designs, the bracket fails to contain the adhesive to relevant areas during the bonding process, thus also requiring monitoring and cleanup. Additionally, in many conventional brackets, the bonding base of the bracket may not be designed for relatively easy removal of the bracket from the tooth. In this regard, the bracket may not include a convenient feature that cooperates with a de-bonding tool for removing the bracket from the tooth. Furthermore, some designs fail to include any features that facilitate the bond between the bracket and tooth so as to result in a more reliable bond therebetween.

FIGS. 6, 7, and 10 illustrate the bonding base 33 of the orthodontic bracket 10 designed to address these and other shortcomings of conventional brackets. In one aspect, the bonding base 33 includes a lingually-extending lip 150 along at least a portion of the periphery 152 of the bonding base 33. In one embodiment, the lip 150 extends along substantially the entire periphery of the bonding base 33. As shown in FIGS. 6 and 7, the lip 150 defines the inner side walls 154 of an open well or cavity 156. Bonding adhesive is adapted to be disposed within the cavity 156 when the bracket 10 is to be bonded to the tooth. The side walls 154 bound the adhesive and prevent or reduce the likelihood of the adhesive from escaping beyond the periphery 152 of the bonding base 33. Thus, the time, expense and aggravation of cleaning up the adhesive is eliminated or reduced.

In addition to containing the bonding adhesive within the periphery 152 of the bonding base 33, the configuration of the lip 150 may provide other benefits. For example, as illustrated in FIG. 11, the corner 158 between an outer side wall 160 of bonding base 33 and the outer side wall 162 (e.g., occlusal, gingival, mesial, and/or distal sides) of the pad 32 may be configured to facilitate removal of the orthodontic bracket 10 from the tooth. In this regard, the corner 158 is radiused or chamfered so as to provide a small gap 164 between the tooth and bracket 10 along the periphery 152 of the bonding base 33. In one embodiment, for example, the corner 158 is radiused with a radius of curvature between approximately 0.005 inch and approximately 0.010 inch. Those of ordinary skill in the art will appreciate that the radius of curvature may be smaller or larger than this range depending on the specific application. The gap 164 not only serves as a crack initiator during a de-bonding process, but also provides a purchase point for a tool, shown schematically at 166, used during the de-bonding process.

In addition to the above, the inclusion of lip 150 on bonding base 33 may further provide for tailoring the de-bonding strength of the bracket 10 from the tooth. In this regard, the particular lip geometry may affect the bond strength in predictable ways, such that the lip geometry may be specifically configured to provide a desired debond strength. In particular, the height of the lip 150, the thickness of the lip 150, and/or the configuration of inner side wall 154 (e.g., smooth, wavy, grooved, etc.) may affect debond strength. Additionally, the configuration of the corner 158 (e.g., radius of curvature) may affect the amount of force an orthodontist applies to a tool for removing the bracket 10 from the tooth.

Furthermore, the bonding base 33 may include additional features for enhancing the bond between the bracket 10 and tooth. In this regard, and as shown in FIG. 10, the bonding base 33 may include a plurality of pegs or posts 168 thereon for improving bond strength. The posts 168 increase the contact area between the adhesive and the bracket and thereby increase bond strength. Additionally, the posts 168 may be further configured to increase the bond strength. For example, the posts 168 may be flattened or deformed at an outer end thereof so as to create undercuts (not shown). Adhesive fills the undercuts to, in essence, create a mechanical lock between the bonding base 33 and the adhesive.

In one embodiment, the posts 168 may be integrally formed with the bonding base 33. For example, the orthodontic bracket 10 may be formed from a ceramic material, as discussed above, using a ceramic injection molding (CIM) process. One technique for forming such posts 168 includes laser shaping the bonding base 33 during the green or brown state of the CIM process. An exemplary laser shaping technique is more fully disclosed in U.S. Publication Nos. 2006/0163774 and 2006/0166159, the disclosures of which are incorporated by reference herein in their entirety. In addition to laser shaping the bonding base 33 to form posts 168, those of ordinary skill in the art may recognize other techniques for forming posts 168.

Other features in addition to, or in lieu of, posts 168 may be included to increase the bond strength between the bracket 10 and tooth via a suitable adhesive. Such features may include forming projections, recesses, undercuts, etc. in the bonding base 33. For example, another technique includes ball basing the bonding base 33. Ball basing uses a monolayer of small, generally spherical particles on the bonding base to effectively create undercuts. As more fully disclosed in U.S. Pat. No. 5,071,344, the disclosure of which is incorporated by reference herein in its entirety, a layer of adhesive is applied to the bonding base through, for example, a brushing or spraying technique. Thereafter, small, generally spherical particles (shown in phantom in FIG. 12) are either sprinkled on the bonding base 33, or the bracket 10 is tamped into a pile of particles, such that a relatively dense monolayer of particles is provided. The bracket is then heated in a furnace to diffusion bond the particles to the bonding base 33.

Figure 12:
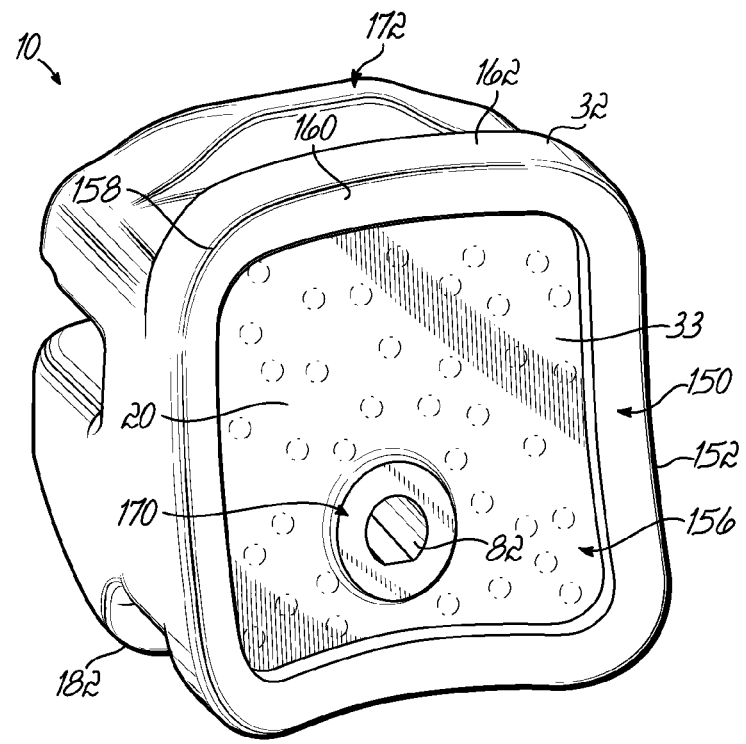
FIG. 12 is a rear perspective view of a self-ligating orthodontic bracket in accordance with an alternative embodiment.

As shown in FIG. 12, the bore 82 for receiving spring pin 78 is open to bonding base 33. As noted above, during assembly, the spring pin 78 is inserted into bore 82 via this opening. Manufacturing processes will generally form the bond-enhancing features on bonding base 33 prior to insertion of spring pin 78 in bore 82. Accordingly, it may be desirable to keep adhesive and other material, such as the particles used in a ball basing technique, from entering into bore 82. In this regard, the bonding base 33 may include a lingually-extending lip 170 about the opening to bore 82. For example, the lip 170 may be positioned along the periphery of the bore 82 or radially spaced therefrom by a relatively small amount. The lip 170 prevents or at least reduces the likelihood of adhesive and/or particles from entering bore 82 and perhaps making insertion of spring pin 78 within bore 82 problematic.

Figure 13:
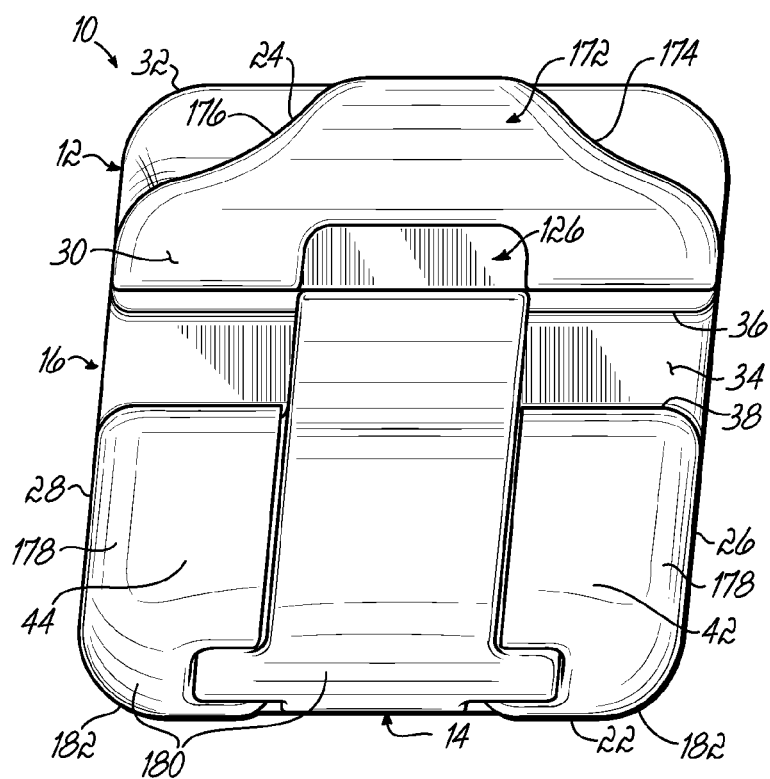
FIG. 13 is a front elevation view of the self-ligating orthodontic bracket shown in FIG. 1.

In still a further aspect, and as illustrated in FIG. 13, the orthodontic bracket 10 may include a single gingival tie wing 172 and two occlusal tie wings 182 that facilitate coupling of the bracket to other adjacent orthodontic devices using ligatures, elastic bands, or other connecting members known in the art. A single tie wing 172 may be desirable, compared to the more traditional two tie wing design, because it provides less surface area for food or other material in the oral cavity to bear on. As a result, bond reliability may be improved. The tie wing 172 may be centrally located on the bracket body 12 in the mesial-distal direction. As a result, mesial and distal sides 174, 176 of the wing 172 may have a sloped or scalloped configuration, and therefore be inclined in a gentle and smooth manner. Such shaping of the tie wing 172 enhances the comfort of orthodontic bracket 10.

Further in this regard, manufacturers of orthodontic brackets continually seek improvements to bracket designs that provide greater comfort to the patient. For example, many conventional orthodontic brackets include labial sides that are irregular or discontinuous. In some situations, these irregularities may cause discomfort to the patient as, for example, soft oral tissue repeatedly engages the labial surface of the bracket. The orthodontic bracket 10 addresses such shortcomings by configuring the surface of the bracket 10 in a smooth and continuous manner. Thus, the edges or transitions between adjacent sides of the bracket may be characterized by one or more curves each having a generally large radius of curvature.

For example, the transitions, generally shown at 178, between the labial side 30 and the mesial and distal sides 26, 28 may be generally arcuate and have a radius of curvature of between approximately 0.015 inch and approximately 0.025 inch. Additionally, the transition 180 between the labial side 30 and occlusal side 22 may also have a radius of curvature in the range provided above. Moreover, the edges of the tie wing 172 may also be smoothed by using a relatively large radius of curvature thereat. The smooth transitions between adjacent sides of the bracket result in an overall improvement to the comfort of the orthodontic bracket 10.

Figure 14:
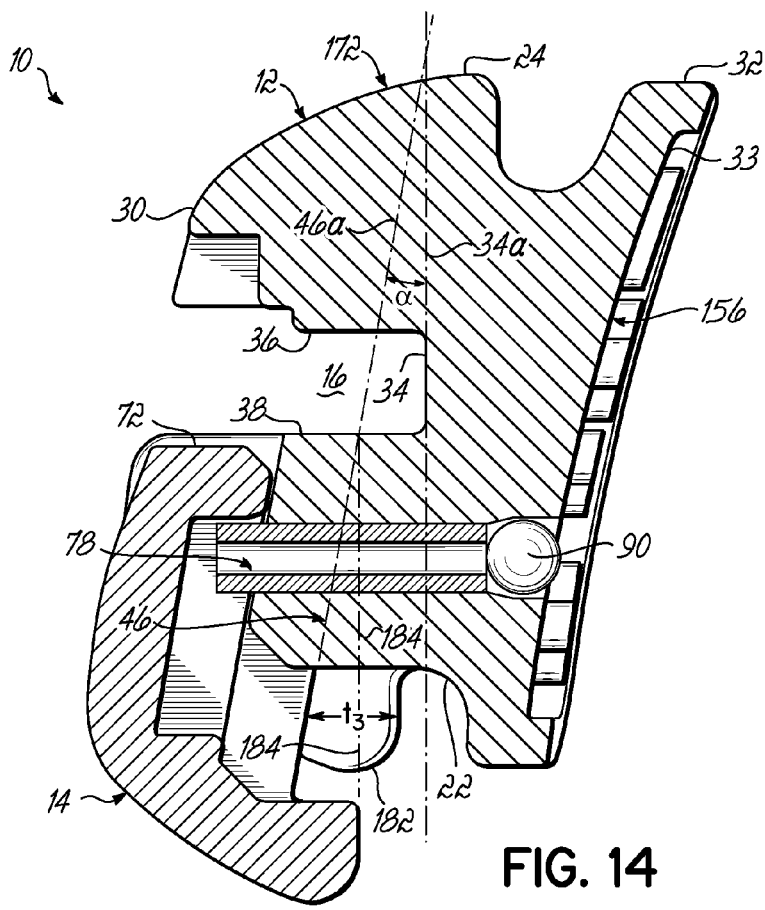
FIG. 14 is a cross-sectional view similar to FIG. 7 of the orthodontic bracket shown in FIG. 1 taken generally along line 7-7.

As shown in FIG. 14, another feature includes configuring orthodontic bracket 10 such that ligating slide 14 moves along slide engagement track 46 at an angle ☐ relative to the base surface 34 of archwire slot 16. In this regard, engagement track 46 extends generally along a translation plane 46a that is acutely angled relative to a base plane 34a associated with the base surface 34. Such an angled feature was disclosed in U.S. Pat. No. 7,267,545 for molar self-ligating brackets. In molar applications, the angled feature helps avoid contact between the ligating member and the surrounding gingiva. As illustrated in FIG. 14, the angled nature of slide engagement track 46 in orthodontic bracket 10 provides for an increase in the wall thickness $t_3$ of the occlusal tie wings 182 (one shown) relative to the more traditional parallel engagement configuration (shown as a phantom line 184). Accordingly, the strength of the occlusal tie wings 182 is increased. Angling of the slide 14 to achieve an increase in tie wing thickness may be particularly relevant in high torque brackets. Moreover, in high torque applications, the angled nature of slide engagement track 46 also provides an increase in the clearance underneath the tie wing 182. Thus, various connecting members (e.g., ligatures, O-rings, power chains, etc.) may be more securely coupled to bracket 10.

Figure 15:
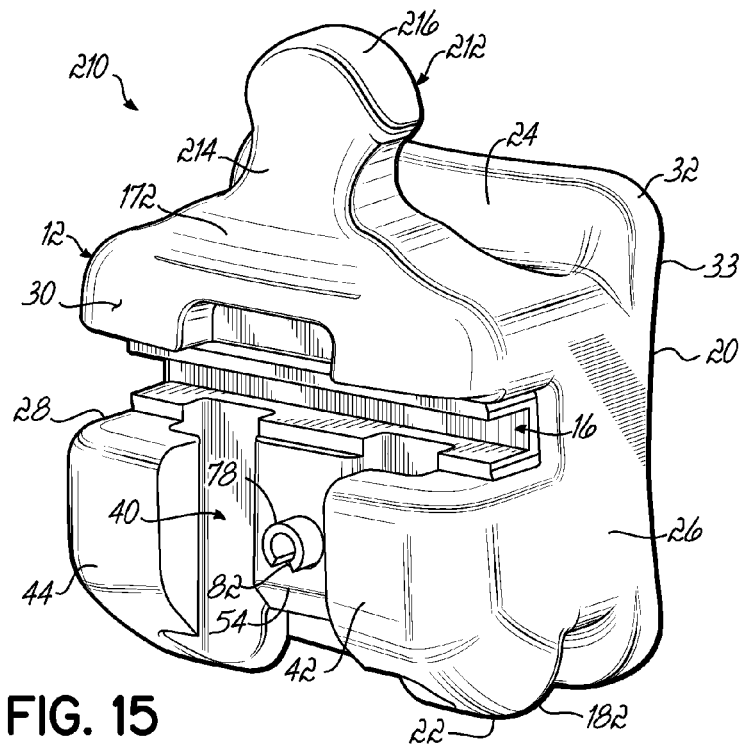
FIG. 15 is a perspective view of a self-ligating orthodontic bracket in accordance with another embodiment of the invention.

FIG. 15, in which like reference numerals refer to like features in FIGS. 1-14, illustrates an orthodontic bracket 210 in accordance with an alternative embodiment. Orthodontic bracket 210 is similar to orthodontic bracket 10 and only the differences will be discussed in detail. As an initial matter, the bracket 210, as shown, is also configured and described from a reference frame of being applied to a tooth on the upper jaw. However, as discussed above, those of ordinary skill in the art will appreciate that the invention is not so limited. In many applications, it is desirable to include a hook with a dental bracket for coupling to an adjacent orthodontic device. Typically, the hook is a separate element that is permanently affixed to the bracket body. Alternatively, the hook may be an auxiliary device that is temporarily or releasably coupled to the bracket body. This may be achieved, for example, through the use of an auxiliary slot (e.g., vertical slot) formed in the bracket body that receives the shaft of a hook therein (not shown).

As shown in FIG. 15, in one embodiment, the orthodontic bracket 210 may include a hook, generally shown at 212, integrally formed with the bracket body 12. More particularly, in one embodiment, the hook 212 may include a stem 214 that extends generally in a gingival direction from the tie wing 172 and terminates in an enlarged head 216. The combination tie wing/hook feature allows orthodontic bracket 210 to retain both of these capabilities but in a more efficient manner that obviates the need for separate components or auxiliary slots formed through the bracket body 12. The invention, however, is not so limited as the hook 212 may be integrally formed with the bracket body 12 at locations other than tie wing 172 (not shown) depending on the specific application and/or desires of the orthodontist. For example, a hook 212 may be integrally formed with a bracket body that has no tie wings (e.g., molar brackets).

Figure 16:
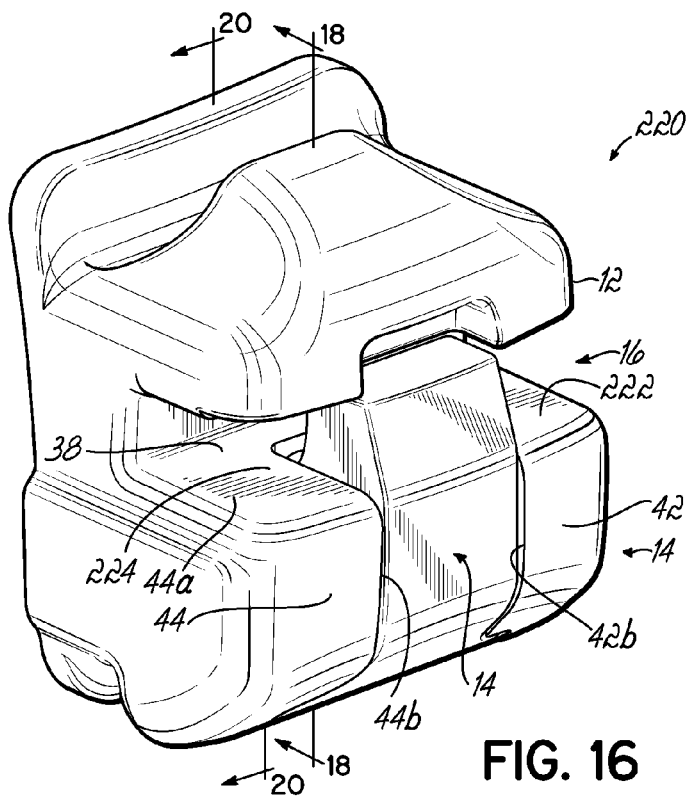
FIG. 16 is a perspective view of a self-ligating orthodontic bracket in accordance with one embodiment of the invention with a ligating slide shown in a closed position.
Figure 17:
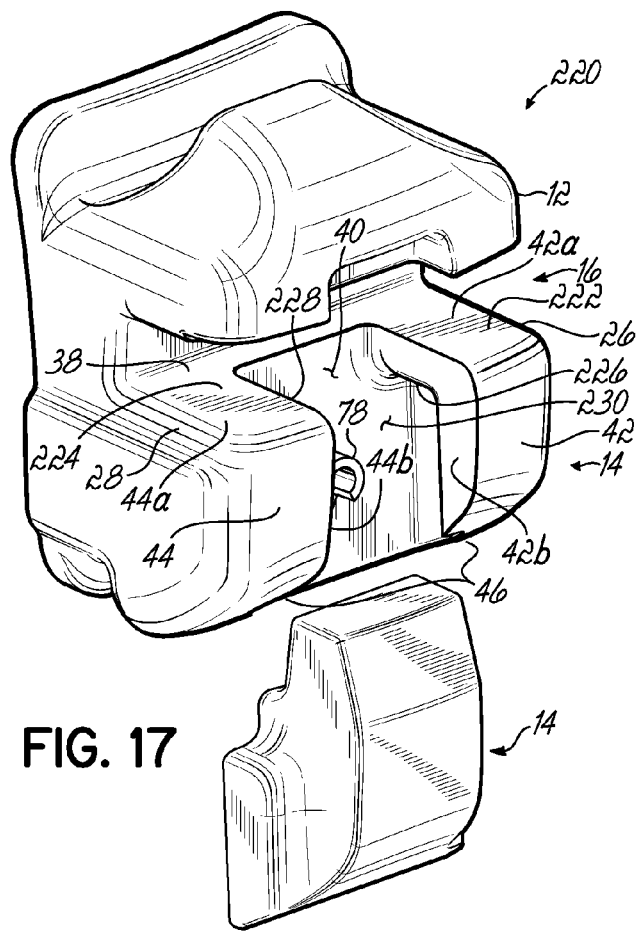
FIG. 17 is a perspective view of the self-ligating orthodontic bracket shown in FIG. 16 with the ligating slide shown disassembled from the bracket body.

FIGS. 16 and 17, in which like reference numerals refer to like features in FIGS. 1-14, illustrate an orthodontic bracket 220 in accordance with an alternative embodiment. Orthodontic bracket 220 is similar to orthodontic bracket 10 and only the differences will be discussed in detail. Like the brackets 10 and 210, the orthodontic bracket 220 is also configured and described from a reference frame of being applied to a tooth on the upper jaw. As described above, bracket designs that limit or stop gingival movement of the ligating slide 14 relative to the bracket body 12 using only the pin 78 may be susceptible to premature failure, because much of the load imposed on the ligating slide 14 is transmitted to the bracket body 12 primarily through the pin 78. Due to the small contact area between the pin 78 and the ligating slide 14, the magnitude of these loads may be sufficient to shear, notch, or otherwise damage the pin 78, the ligating slide 14, and/or the bracket body 12. By increasing the area of contact between the ligating slide 14 and bracket body 12, the imposed loads are dispersed over a larger area. In other words, the imposed loads are distributed from the slide 14 directly to the body 12 rather than to the body 12 via the pin 78. As described above with reference to the orthodontic bracket 10, the area of contact may be increased by the contact of the tab 104 with the cutout 60. In other embodiments, the area of contact between the ligating slide 14 and the bracket body 12 may be increased by additional or alternative features.

For example, and with reference to the exemplary embodiment shown in FIGS. 16 and 17, the orthodontic bracket 220 includes intervening walls 222, 224 integrally formed with the bracket body 12. As shown best in FIG. 17, support surface 40 carries intervening walls 222, 224 which are positioned adjacent to the guides 42, 44 on the mesial and distal sides 26, 28 of surface 40. Therefore, generally, the intervening walls 222, 224 partially close off mesial and distal sides of the slide engagement track 46 adjacent the archwire slot 16. In particular, in the embodiment shown, the mesial intervening wall 222 projects distally from the first leg 42a of guide 42, and the distal intervening wall 224 projects mesially from the first leg 44a of guide 44. Thus, the intervening walls 222, 224 form contacting or stop surfaces in the slide engagement track 46. The stop surfaces, like stop surfaces described above, limit movement of the ligating slide 14 in the gingival direction and increase the contact area between the ligating slide 14 and the bracket body 12 when the ligating slide 14 is in the closed position (as shown in FIG. 16). In particular, the respective intervening walls 222, 224 form contacting surfaces or shoulders 226, 228 on the mesial and distal sides 26, 28 of the slide engagement track 46. The shoulders 226, 228 abut a portion of the ligating slide 14 as described below. Furthermore, these contacting surfaces may operate alone or in conjunction with any of the contacting surfaces as set forth above, or below, to distribute loads on the slide 14 to the bracket body 12.

Further, in regard to distribution of loads imposed by the archwire and with reference to FIG. 17, the intervening walls 222, 224 extend from the support surface 40 to the second leg 42b, 44b of the respective guide 42, 44, or, in other words, the intervening walls 222, 224 form gussets that distribute loads imposed by the archwire on the guides 42, 44 to the body 12. Specifically, the gussets reduce the torque experienced by the ears of each guide 42, 44. This configuration improves the strength and rigidity of the respective guide 42, 44. While the intervening walls 222, 224 are shown as extending the full mesial-distal width of the respective second legs 42b, 44b, the walls 222, 224 need not extend the full mesial-distal width of the guides 42, 44 and still transmit loads between the slide 14 and the body 12. For example, the mesial intervening wall 222 may project distally from the first leg 42a of the mesial guide 42 to a distance that is less than the full distal projection of the second leg 42b of the guide 42. Similarly, the distal intervening wall 224 may project less than the full mesial-distal distance of the second leg 44b of guide 44.

In one embodiment, as shown in FIG. 17, the intervening walls 222, 224 are adjacent to or form a portion of the archwire slot 16, and, more particularly, form a portion of the slot surface 38. The intervening walls 222, 224, however, may be placed occlusally of the archwire slot 16. In this regard, the intervening walls 222, 224 may be configured to be flush with the slot surface 38 or may be spaced occlusally of the slot surface 38.

As a consequence, and as shown in FIG. 17, the intervening walls 222, 224 may complement or replace features found in brackets 10 and 210. For example, the raised boss 54 (shown in FIG. 4, for example) may not be present. Those of ordinary skill in the art will observe, however, that the bracket body 12 may be configured with both the intervening walls 222, 224 and the raised boss 54. In this embodiment, that is, without the boss 54, the slide engagement track 46 may include a single groove 230 rather than the two groves 56, 58 separated by the boss 54. The ligating slide 14 may then have complementary features to the single groove 230, as described below.

Similar to the absence of the raised boss 54, the cutout 60, also described above and shown in FIG. 4, may not be present. As shown in FIG. 4, the cutout 60 forms a stop surface in the bracket body 12. The cutout 60 cooperates with the tab member 104 on the ligating slide 14 shown for example in FIG. 5. However, as shown in FIG. 17, where the body 12 includes intervening walls 222, 224, the bracket body 12 may not include the cutout 60 since the intervening walls 222, 224 provide, at least in part, stop surfaces. Consequently, the ligating slide 14 may not include tab 104, as described more fully below.

With reference to FIG. 18, in one embodiment, the bore 82 is moved away from the archwire slot 16 by elongating the body 12 by about 0.010 inch (shown, for example, by the distance between phantom line or pad 32' of bracket 10 and pad 32 of the bracket 220) and providing tapered sides 230, 232 on occlusal side 22 as compared to occlusal side 22' for the body 12 of bracket 10. In particular, the bore 82 of the bracket 220 is moved occlusally away from the archwire slot 16. The relative bore of the bracket 10 of FIG. 1 is labeled 82'.

Similarly, the relative locations of the occlusal side of the bracket 10 and bracket 220 are illustrated by comparing occlusal sides 22 and 22', respectively. Additionally, in the absence of the cutout 60, the bracket body 12 has a single occlusal tie wing 234 rather than mesial and distal occlusal tie wings 182 spaced apart by the cutout 60. The single occlusal tie wing 234 may extend nearly the full width of the bracket body 12. This configuration may ease attachment of connecting members (not shown) therein, may increase the strength of the body 12, as well as, reduce the sites available for plaque and/or food buildup.

Similar to the ligating slide 14 shown in FIGS. 1 and 2, the ligating slide 14 depicted in FIGS. 16, 17, and 19 includes mesial and distal portions 62, 64 that do not extend the full gingival-occlusal extent of the ligating slide 14. However, with reference to FIG. 19, the mesial and distal portions 62, 64 define shoulders 236, 238 configured to engage bracket body 12 prior to the spring pin 78 bottoming out on the occlusal end 112 of retaining slot 80. Specifically, the shoulders 236, 238 of the mesial and distal portions 62, 64 abut a portion of the intervening walls 222, 224, such as the shoulders 226, 228, when the ligating slide 14 is moved to the closed position.

To this end, the shoulders 236, 238 or contacting surfaces of mesial and distal portions 62, 64 include a distal engaging portion 240 and a mesial engaging portion 242 that respectively engage engaging portions of the body 12, and, in particular, engage portions of walls 222, 224, like shoulders 226, 228. As set forth above and with reference to FIG. 17, the surface contact between the engaging portions of the ligating slide 14 and the engaging portions of the bracket body 12 increase the area of contact between the body 12 and slide 14 thereby distributing more load directly between the slide 14 and body 12.

Furthermore, while no portion of the mesial portion 62 or of the distal portion 64 may extend past intervening walls 222, 224 or form a portion of the slot surface 38 (as shown in FIG. 16), a portion of one or both of the mesial and distal portions 62, 64 may be adjacent to or form a portion of the slot surface 38 similar to the platform surfaces 74, 76 described above and shown in FIGS. 2 and 5. For example, partial platform surfaces (not shown) may be present where the intervening walls 222, 224 extend along only part of the mesial-distal extent of the guides 42, 44. This configuration would amount to a combination of the ligating slide having both shoulders 234, 236 and platform surfaces 74, 76 (shown in FIG. 5).

With reference to the ligating slide 14 shown in FIGS. 19 and 19A, the ligating slide 14 has a substantially planar lingual side 94b that slidably cooperates with the single groove 230 described above. Specifically, where the raised boss 54 is absent, the ligating slide 14 does not include the cavity 96 shown, for example, in FIG. 5. In other words, the retaining slot 80 may be formed directly in the lingual sides 94a, 94b rather than being formed within cavity 96.

In addition and with reference to FIGS. 18, 19 and 19A, where the bore 82 is moved nearer the occlusal side 22 of the body 12, as described above, the retaining slot 80 may likewise be formed nearer to the occlusal side of the ligating slide 14. Advantageously, rather than having the retaining slot 80 formed in the slot covering portion 146, as shown in FIG. 6, the retaining slot 80 is formed entirely within the bracket engaging portion 144. In one embodiment, the gingival end 116 of the retaining slot 80 is positioned occlusally of the corner 149. Accordingly, mesial-distal cross sections taken along planes oriented generally in the lingual-labial direction through the slot covering portion 146 do not intersect the retaining slot 80. Positioning of the retaining slot 80 away from the slot covering portion 146 may improve load carrying capability or rigidity of the slide 14 due to the gain in material in this portion of the slide 14. Moreover, moving the retaining slot 80 into the bracket engaging portion 144 has additional advantages. For example, referring to FIG. 20, in this regard, the retaining slot 80 is not exposed to the archwire slot 16 when the ligating slide 14 is in the closed position.

Figure 20:
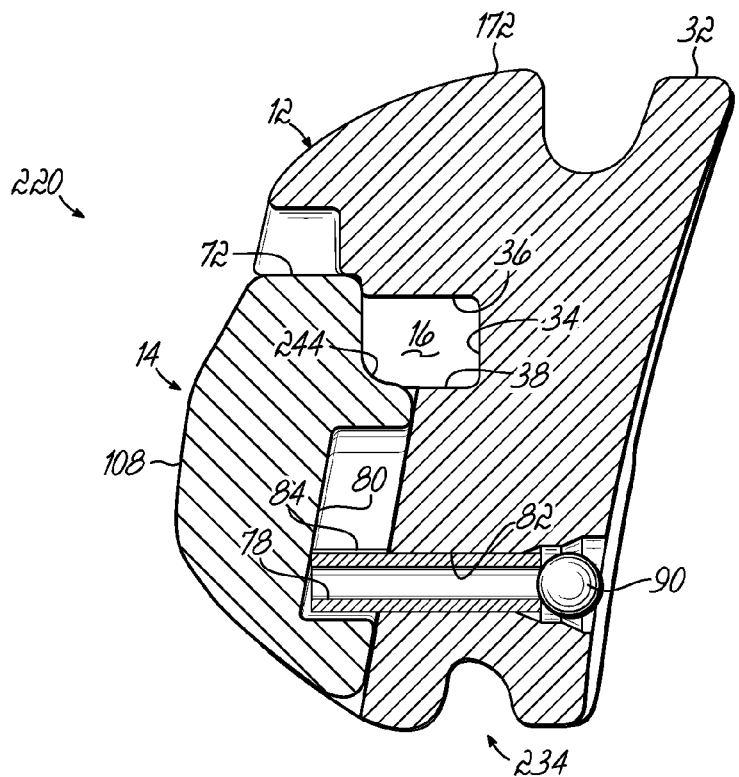
FIG. 20 is a cross-sectional view of the orthodontic bracket shown in FIG. 16 taken generally along line 20-20.

In further regard to the exemplary ligating slide 14 shown in FIGS. 19 and 19A, a central platform surface 244 is formed in the central portion 66 of the ligating slide 14. For example, in the absence of the raised boss 54 and the cavity 96, shown in FIGS. 4 and 5, respectively, the central platform surface 244 may include a surface that faces in the gingival direction and may be formed between the corner 149 and the lingual side 94b. With reference to FIG. 20, when the ligating slide 14 is in the closed position, the central platform surface 244 may be adjacent to or form a portion of the archwire slot 16, and more particularly, form a portion of the slot surface 38.

Figure 21:
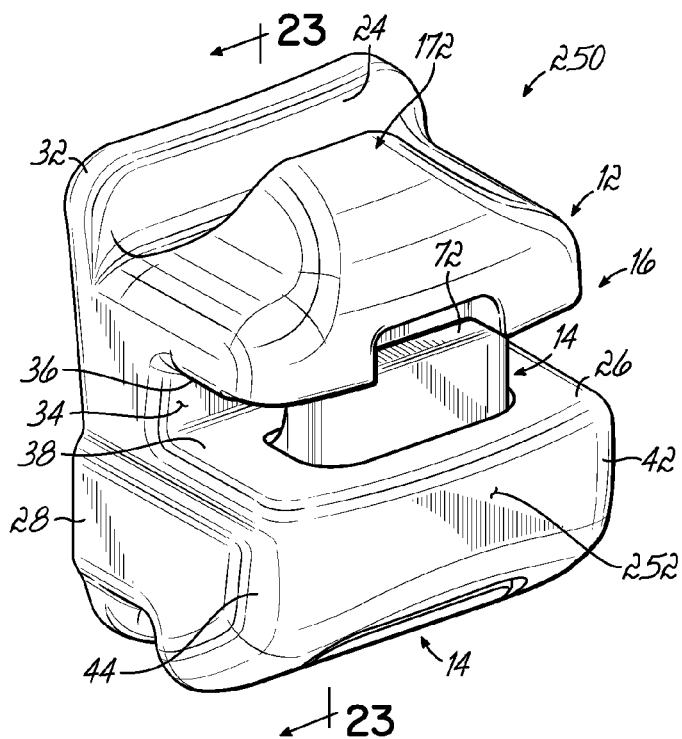
FIG. 21 is a perspective view of a self-ligating orthodontic bracket in accordance with one embodiment of the invention with a ligating slide shown in a closed position.
Figure 22:
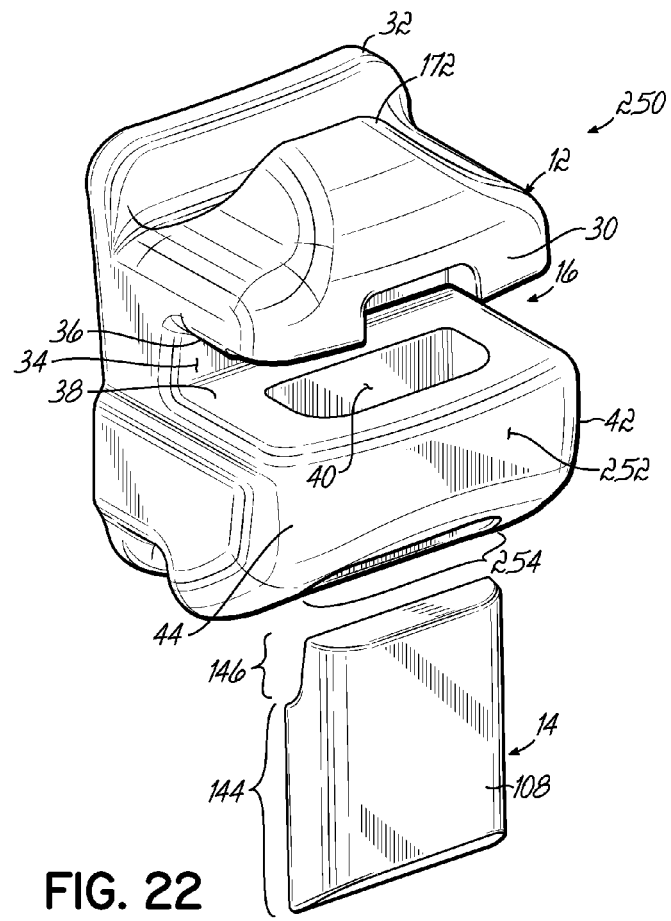
FIG. 22 is a perspective view of the self-ligating orthodontic bracket shown in FIG. 21 with the ligating slide shown disassembled from the bracket body.

In another exemplary embodiment, and with reference to FIGS. 21 and 22 in which like reference numerals refer to like features in FIGS. 1-14, an orthodontic bracket 250 includes bracket body 12 having a bridge 252 connecting opposing ears or guides 42, 44. Like the brackets 10, 210, and 220, the bracket 250 is also configured and described from a reference frame of being applied to a tooth on the upper jaw. As best shown in FIG. 22, in one embodiment, the bridge 252 joins the opposing guides 42, 44 such that support surface 40; guides 42, 44; and bridge 252 collectively define a D-shaped engagement track 254 for supporting and guiding the ligating slide 14 between open and closed positions. Generally, by extending between opposing mesial and distal portions of the body 12 labially of the slide engagement track 46, the rigidity and/or strength of the body 12 may be improved. Furthermore, the bridge 252 may enclose or encapsulate at least a portion of the bracket engaging portion 144 of slide 14 and may, accordingly, separate a portion of that side (i.e., the labial side 108) of the ligating slide 14 from the buccal mucosa.

Not only is the lingual side 108 of the bracket engaging portion 144 separated from buccal mucosa surfaces, the lingual side 108 of the slot engaging portion 146 is also separated from the buccal mucosa. For example, and with reference to FIG. 23, when the slide 14 is in the closed position, the labial side 108 of the slide engaging portion 146 may be positioned lingually of the labial side 30 of the body 12 (e.g., closer to the pad 32). The relative difference in position between the two sides (30 and 108) creates an overhang 256. The overhang 256 may also prevent or reduce contact between the labial side 108 of the slot covering portion 146 and the buccal mucosa or food which would tend to force the ligating slide 14 toward the open position.

Figure 23:
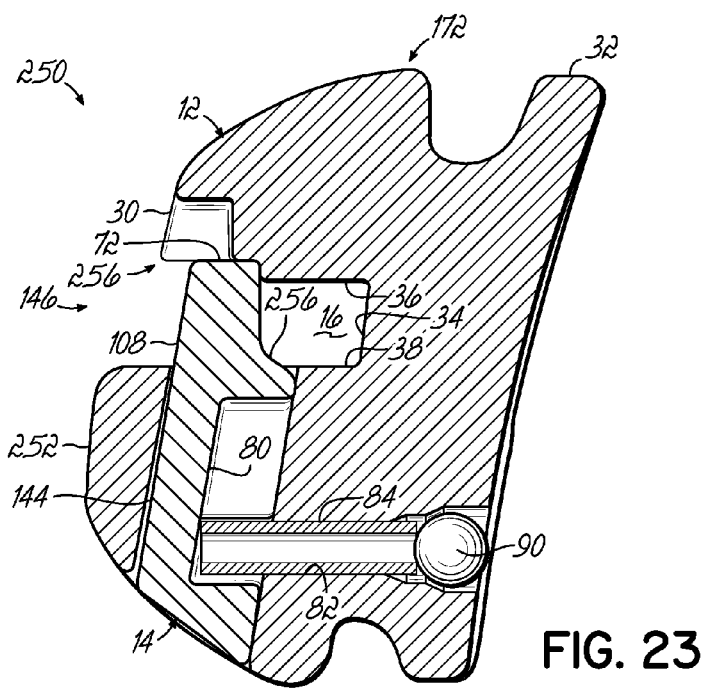
FIG. 23 is a cross-sectional view of the self-ligating orthodontic bracket shown in FIG. 21 taken generally along line 23-23.

For example, when the ligating slide 14 is in the closed position (as shown in FIGS. 21 and 23), loads tending to pull an archwire (not shown) from archwire slot 16, such as normal corrective loads necessary for tooth movement, push a portion of the bracket engaging portion 144 outward where it is captured by the bridge 252. Since the bridge 252 extends between the guides 42, 44, it distributes loads directly from the ligating slide 14 to the body 12.

With reference to FIGS. 22, 23, 24, and 24A, in one embodiment, the ligating slide 14 has a substantially D-shaped cross section or another cross section that is configured to slidably engage the engagement track 254 defined by the bridge 252; the guides 42, 44; and the support surface 40. The lingual side 94b of the bracket engaging portion 144 is substantially planar and is configured to slidably cooperate with the support surface 40. The lingual side 94a of the slot covering portion 146 is offset from the lingual side 94b by the corner 149. The corner 149 extends the mesial-distal width of the ligating slide 14, and thus may form an edge or a platform surface 256, like central platform surface 240. However, the platform surface 256 extends the mesial-distal width of the ligating slide 14. Furthermore, the platform surface 256 may be adjacent or form a portion of the archwire slot 16, and more particularly, form a portion of the slot surface 38.

Figure 24:
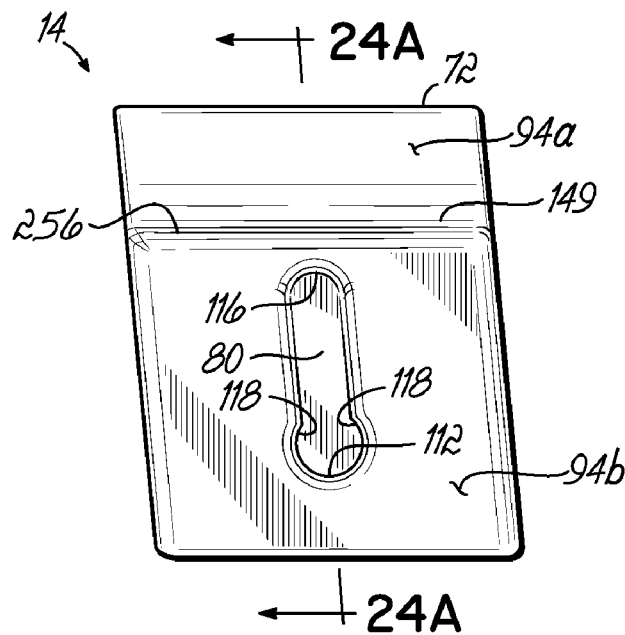
FIG. 24 is a rear elevation view of the ligating slide shown in FIGS. 21 and 22.
Figure 24A:
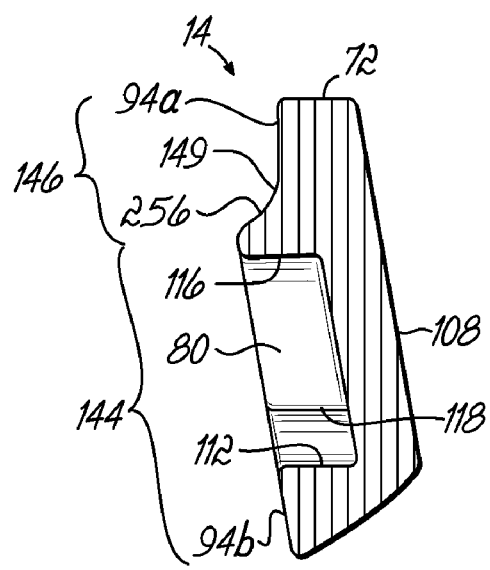
FIG. 24A is a cross-section view of the ligating slide shown in FIG. 24 taken along line 24A-24A.

As with the ligating slide 14 illustrated with bracket 220, the gingival end 116 of the retaining slot 80 may be formed fully within the bracket engagement portion 144. For example, the gingival end 116 of the slot 80 may be formed occlusally of the slot covering portion 146. Or, in another example, the gingival end 116 of the slot 80 as shown in FIG. 24A may be formed occlusally of the corner 149. Consequently, mesial-distal cross sections taken along planes oriented generally in the lingual-labial direction through the slot covering portion 146 may not intersect the retaining slot 80. As set forth above, where the retaining slot 80 is formed fully within the bracket engagement portion 144, the slide 14 may exhibit improved strength. Furthermore, the slot 80 may not be exposed to the archwire slot 16 when the ligating slide 14 is in the closed position (shown in FIG. 23). Thus, any food or other debris that finds its way into the archwire slot 16 will not become lodged in the retaining slot 80, which would possibly obstruct movement of the slide 14 to the open position.

With reference generally to any of the orthodontic brackets shown in FIGS. 1-22, but specifically to the orthodontic bracket 10, the bracket body 12 comprises a polycrystalline ceramic, for example alumina or aluminum oxide ($Al_2O_3$). And, in another embodiment, the bracket body 12 and the ligating slide 14 comprise the polycrystalline ceramic. The bracket body 12, and optionally the ligating slide 14, comprising the polycrystalline ceramic more readily resists fracture when loaded with tensile and flexural stresses, such as those generated by engagement with the archwire 18 or those that normally occur during orthodontic treatment. By way of example, and not limitation, orthodontic brackets described in FIGS. 1-22 can be formed from the polycrystalline ceramic described herein. It will be appreciated that while self-ligating brackets are shown and described herein, embodiments of the present invention are not limited to self-ligating brackets.

As is known in the art, ceramic brackets tend to be brittle and too often fail during orthodontic treatment. Of course, bracket failure is problematic. For instance, a fractured bracket renders tooth movement ineffective. A more troubling problem is that pieces of the fractured bracket may be ingested or inhaled if fracture occurs while the bracket is in the patient's mouth. As will be described more fully below in conjunction with the examples, the inventors have discovered that the polycrystalline ceramic having a grain size distribution described, in part, by an average grain size in the range of larger than 3.4 μm to about 6 μm has unexpectedly high fracture toughness. For example, the polycrystalline ceramic having an average grain size in the range of larger than 3.4 μm to about 6 μm has an average fracture toughness of at least about 3.85 MPa·m$^{1/2}$ and, in a further example, the polycrystalline ceramic having an average grain size between about 4 μm and about 4.3 μm has an average fracture toughness that exceeds about 5.0 MPa·m$^{1/2}$. By comparison, the average fracture toughness of polycrystalline alumina having an average grain size of 43 μm is about 3.28 MPa·m$^{1/2}$.

For example and with reference to FIG. 1, the orthodontic bracket 10 comprising the polycrystalline ceramic described herein advantageously reduces the risk of patient ingestion or inhalation of portions of a fractured bracket, and the patient endures fewer, if any, bracket replacements. Overall, the orthodontic bracket 10 comprising the polycrystalline ceramic permits orthodontic treatment to proceed more quickly. In addition, the orthodontic bracket 10 is translucent such that the patient is less self-conscious during treatment.

In one embodiment, the orthodontic bracket 10 is prepared by injection molding a ceramic powder and binder mixture to form a bracket body. The binder may then be removed from the injection molded body by heating the injection molded body to a temperature, for example, between 200° C. and 700° C. Following removal of the binder, the injection molded body may then be presintered followed by sintering. By way of example, the ceramic powder may be alumina powder. High purity alumina powder (about 99.95 wt. % alumina) may be presintered at temperatures of between 900° C. and 1,200° C. followed by sintering at between 1,400° C. and 1,800° C. In other embodiments, the presintered injection molded body may be hot-isostatically pressed (HIPed). For example, a presintered injection molded body of alumina may be hot-isostatically pressed (HIPed) at between about 1,300° C. and about 1,600° C. with an applied pressure of about 68 to about 207 MPa.

In other embodiments, following sintering or HIPing, the bracket body 12 is annealed, i.e., heated to a temperature and held for a time sufficient to further modify the grain size distribution. Modification of the grain size distribution may occur at temperatures of about 1300° C. or higher for alumina. However, higher or lower temperatures than 1300° C. may modify the grain size distribution depending on the time the bracket body is held at that specific temperature. By way of example, the bracket body may be held at about 1300° C. for about 1 hour. In addition, the bracket body 12 may be heated in a variety of atmospheres including, for example hydrogen ($H_2$), nitrogen ($N_2$), oxygen ($O_2$), or argon (Ar).

To assess the performance of a ceramic material, the flexural strength of the material may be measured with a three-point bend setup. Samples for three-point bend testing are generally in the form of a rectangular bar. In a three-point bend setup, a bar of the material is supported on one side at two locations along the bar's length. Each support location is near one of the bar's ends. The distance between the opposing supports is referred to as the support span. A load is applied to the bar on the surface opposite to and centered between the supports. The load is gradually increased until the bar fractures. This arrangement (i.e., two supports on one side and a load applied between the supports on the opposing side) produces tensile stresses in one surface of the bar. The flexural strength may be calculated based on the dimensions of the bar and the load at the time of fracture according to the well-known equation:

$$\sigma = \frac{3PS}{2wt^2}$$

where σ is the flexural strength, P is the load at fracture, S is the support span, w is the bar width, and t is the bar thickness.

Figure 25:
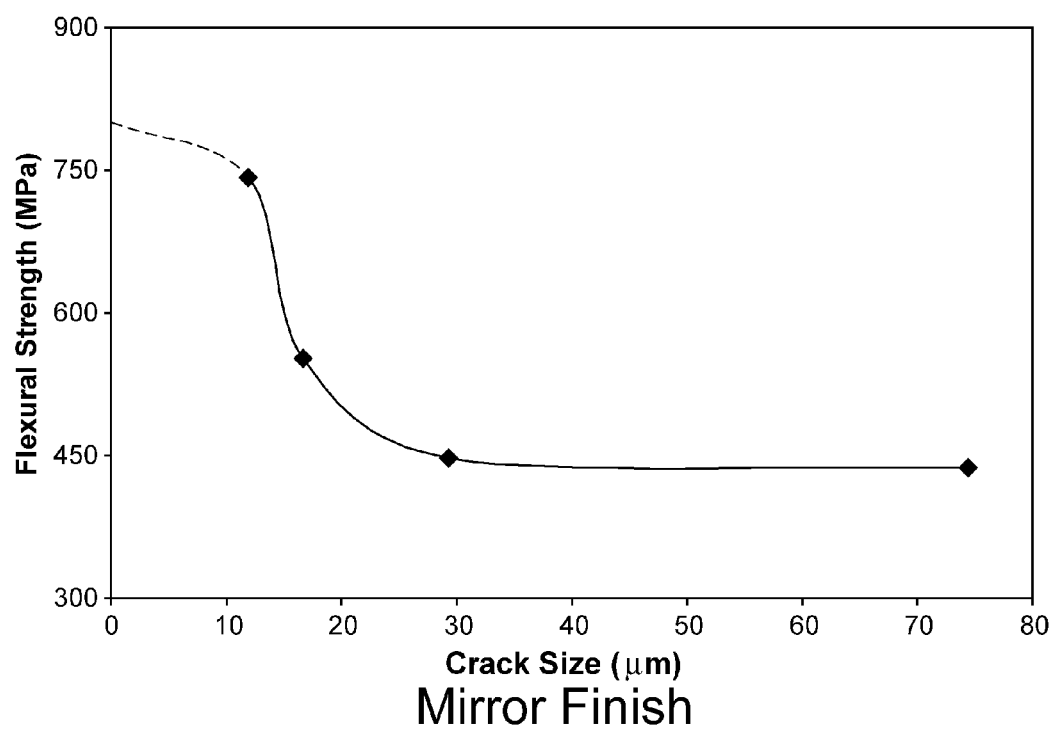
FIG. 25 is a graph illustrating the effect of surface flaws on the flexural strength of polycrystalline alumina.

The inventors have noted that there are many variables that influence flexural strength of a sample of material. For example, the method of manufacturing, preparation, or handling of the samples for testing or a combination thereof can greatly influence flexural strength as each may create flaws in the surface of the sample. Surface flaws (e.g., microcracks, porosity, surface damage, abnormal grains or another localized microstructural heterogeneity, or foreign inclusions, among others) are known to concentrate or magnify stresses. Magnification of the stresses occurs at each flaw's tip. As such, the localized tensile stress at each flaw's tip is greater than the applied tensile load. When the stress concentrated at the tip of one flaw exceeds the theoretical strength of the material, a crack originating at that flaw will rapidly propagate through the material. Flexural strength measurements, therefore, are inherently influenced by the surface condition of the sample. For example, the inventors measured the flexural strength of polycrystalline alumina having an average grain size of 4.5 μm for different crack sizes which were artificially introduced with a diamond indenter. The sensitivity of flexural strength of polycrystalline alumina to increasing crack size is illustrated in FIG. 25.

In addition, the flexural strength data may also be influenced by any of a number of other factors including, for example, the configuration of the sample, the number of tests performed, and the stress state in the actual bracket compared to the stress state in the sample, among others. In sum, flexural strength data does not necessarily provide an accurate prediction of the performance of ceramic orthodontic brackets in the clinical environment.

Recognizing the fallibility of flexural strength measurements noted above, the fracture toughness of the polycrystalline ceramic described herein was also determined. Fracture toughness is a material property that indicates how a material containing surfaces flaws (e.g., the notch in the notched samples) will respond to tensile stresses, and, in particular, how the bulk of the material is resistant to extension of a crack from the surface flaw. Therefore, unlike flexural strength measurements described above, fracture toughness measurements are a measurement of how the bulk material will respond to stresses in the event of surface imperfections. Taking into account the known factors that influence fracture, fracture toughness measurements provide a more accurate indication of the performance of a polycrystalline ceramic bracket within a clinical environment.

The fracture toughness may be determined by at least two methods. Using the three-point bend setup used for flexural strength measurements, fracture toughness can be calculated from the load at fracture obtained from breaking a bar of the material that contains a flaw or crack of controlled or known size. The fracture toughness may be calculated from the load at fracture according to the equation:

$$K_{IC} = \left(\frac{PS}{wt^{\frac{3}{2}}}\right)\left\{\frac{3}{2}\left(\frac{a}{t}\right)^{\frac{1}{2}} \cdot Y\left(\frac{a}{t}\right)\right\}$$

where $K_{IC}$ is the fracture toughness of the sample under a tensile stress that is oriented perpendicular to a crack, P is the load at fracture, S is the support span, w is the bar width, t is the bar thickness, and $$Y\left(\frac{a}{t}\right) = 1.964 - 2.837\left(\frac{a}{t}\right) + 13.711\left(\frac{a}{t}\right)^2 - 23.250\left(\frac{a}{t}\right)^3 + 24.129\left(\frac{a}{t}\right)^4$$

$$a = \frac{a_1 + a_2 + a_3}{3}$$

where a is the average of three crack length measurements, $a_1$, $a_2$, and $a_3$ or is the depth of a known flaw.

According to another method, fracture toughness can be calculated from Vickers hardness measurements. In this case, the fracture toughness may be calculated according to the following equation, $$K_c = 0.018\left(\frac{E}{HV}\right)^{\frac{1}{2}}\left(\frac{P}{c^{\frac{3}{2}}}\right)$$

where $K_c$ is the fracture toughness, P is the pressing load, E is the modulus, HV is the measured Vickers hardness, and c is one-half of the average of crack length produced by the Vickers hardness indenter.

In one embodiment, the polycrystalline ceramic has a grain size distribution described, in part, by an average grain size in the range of larger than 3.4 μm to about 6 μm. The average grain size may be determined according to the line intercept method. According to this method, a line of known length is drawn on a micrograph of a polished cross section of the material. Intersections between the line drawn and each grain boundary are counted. An average length of the grains is determined dividing the length of the line by the number of intersections counted. The average grain size is calculated according to the equation D=1.56(L), where L is the average length of the grains.

Without intending to be bound by theory, the polycrystalline ceramic's resistance to crack propagation, that is, its fracture toughness, may be influenced by its microstructure, though the effect of a polycrystalline microstructure on crack propagation is not completely predictable. Unlike bodies of a single-crystal ceramic, like sapphire, or isotropic materials, like glass, the fracture toughness of the polycrystalline ceramic may depend on a number of factors including, for example, grain size, grain size distribution, density, and others some of which are not present in single crystals or glass.

In particular, the presence of grain boundaries may affect the crack's propagation direction and/or the crack's mode of propagation. A change in direction and/or change in mode may consume comparatively more energy than the energy required to propagate a crack along a straight path. The mode of crack propagation in polycrystalline ceramics is either intergranular or transgranular or both. Intergranular crack propagation follows the grain boundaries (that is, between grains) while transgranular crack propagation is through the grains. Accordingly, when a propagating crack encounters a grain boundary or a grain, the crack may be forced to change direction, change its mode of propagation (that is, from transgranular to intergranular or vice versa) or change both direction and mode of propagation. By forcing a change in the direction and/or mode of crack propagation, the length of the crack pathway increases, which consumes more energy, and, accordingly, the fracture toughness may increase.

In one embodiment of the present invention, the polycrystalline ceramic, having a grain size distribution described by an average grain size in the range of larger than 3.4 μm to about 6 μm, may force a crack to travel along a path that is longer relative to the polycrystalline ceramics of the prior art. Thus, greater stresses may be required to propagate the crack through the polycrystalline ceramic, as described herein, such that an orthodontic bracket made of the polycrystalline ceramic is characterized by an unexpected resistance to fracture.

In another embodiment, the mixture of both large and small grains in combination with the average grain size may further lengthen the crack's path through the polycrystalline ceramic and further improve the fracture toughness of the polycrystalline ceramic. By way of example, the polycrystalline ceramic having a grain size distribution described by an average grain size in the range of greater than 3.4 μm to about 6 μm may further comprise grains larger than 6 μm in size and grains smaller than 3.4 μm in size.

In one embodiment, further improvement in the fracture toughness of the polycrystalline ceramic may be obtained by a grain size distribution that is not a lognormal distribution. By definition, a lognormal distribution is characterized by a random variable whose logarithm is normally distributed about a mean. As an example, the grain size distribution according to one embodiment is multimodal. In particular, the grain size distribution may be a bimodal distribution.

In one embodiment, a bimodal distribution has a first peak or mode between a grain size of about 1 μm and about 5 μm and a second peak or mode at a grain size larger than about 5 μm. By way of example, the second peak may be between about 5.5 μm and about 7 μm. However, it will be appreciated that the second peak or additional peaks may occur at grain sizes larger than 7 μm. It will also be appreciated that the bimodal grain size distribution does not describe a duplex microstructure. In one embodiment, the average fracture toughness for a polycrystalline ceramic having an average grain size in the range of larger than 3.4 μm to about 6 μm and at least a bimodal grain size distribution is greater than about 4.0 MPa·m$^{1/2}$.

In addition, the inventors have identified that a grain size distribution characterized by having a particular ratio between grains smaller than about 3 μm and larger grains may further enhance resistance to crack propagation. By way of example, the polycrystalline ceramic may have a grain size distribution having up to about 50% of the total number of grains less than about 3 μm in size. By way of further example, the polycrystalline ceramic may have a grain size distribution having the number of grains less than 3 μm in size of at least 10% such that in one embodiment, the number of grains less than 3 μm in size is, for example, between about 10% and about 50% of the total number of grains. In yet another example, the polycrystalline ceramic may be characterized by a grain size distribution having up to about 90% of the total number of grains less than about 10 μm in size. In a further example, the total number of grains less than about 10 μm in size is at least 70%. Therefore, in one embodiment, the total number of grains less than about 10 μm in size is between about 70% and about 90% of the grains.

In terms of volume fraction, according to one embodiment, the polycrystalline ceramic is characterized by a grain size distribution in which grains larger than 10 μm in size may occupy up to 50% of the total volume. By way of example, in one embodiment the grains larger than 10 μm in size occupy at least 10% of the total volume, and in a further example, the grains larger than 10 μm in size may occupy from about 10% up to 50% of the total volume. The volume fraction of grains larger than about 10 μm can be calculated by determining the volume of the grains of a particular size range, multiplying that volume by the total number of grains in that size range, and then dividing by the total volume of all the grains.

With regard to the volume fraction occupied by grains greater than 10 μm, the inventors believe that crack propagation through embodiments of the orthodontic bracket comprising the polycrystalline ceramic may be mixed mode because of the volume fraction ratio described above. That is, if a crack propagates into the polycrystalline ceramic, the polycrystalline ceramic may force the crack to change its mode of propagation one time or many times as it proceeds through the polycrystalline ceramic depending upon what size grain it encounters. For example, the presence of grains less than 10 μm in size may foster intergranular crack propagation. However, a grain that is 10 μm in size or larger may force a crack to change to transgranular propagation. Thus, a mixture of grain sizes, as described, may force a crack to alternate between modes and may, therefore, further lengthen the propagation pathway. Accordingly, the volume fraction of grains described may increase fracture toughness of the polycrystalline ceramic.

As previously noted, the orthodontic bracket 10 is aesthetically pleasing and is, in that regard, translucent. As is known in the art, the translucency of a polycrystalline ceramic, like alumina, is affected by its microstructure. For example, the grain size distribution, the quantity and location of any porosity, and the purity of the starting powder may affect the translucency of the orthodontic bracket 10 as well as the color of the transmitted light. Generally, as the density, grain size, and purity of the polycrystalline ceramic increases, the translucency increases. Thus, a polycrystalline ceramic orthodontic bracket of 100% density, high purity, and large average grain size would permit more light to pass through such that the orthodontic bracket 10 blends in with the underlying tooth color. Translucency can be quantified by measuring the amount of light of a particular wavelength that is transmitted through the polycrystalline ceramic. In one embodiment of the present invention, it is expected that the orthodontic bracket 10 comprising polycrystalline alumina having an average grain size of about 3.5 μm or greater will have a transmittance greater than 45% but less than 85%.

EXAMPLES

In order to facilitate a more complete understanding of embodiments of the invention, the following non-limiting examples are provided.

Two different batches (designated Batch #1 and Batch #2) of specimens of polycrystalline alumina having dimensions of about 25.4 mm by about 38.1 mm by about 1 mm were purchased from Tosoh Corporation, Tokyo, Japan. Twenty-four samples in the form of thin plates approximating the thickness and width of a bracket body were prepared from the Batch #1 specimens by cutting the Batch #1 specimens to the desired dimensions. Similarly, eight samples from Batch #2 were prepared by cutting the Batch #2 specimens to the desired dimensions. Each sample cut from the Batch #1 and Batch #2 specimens had a thickness of about 1.00±0.1 mm, a width of about 3.00±0.01 mm, and a length of about 12.00±0.01 mm.

Figure 26A:
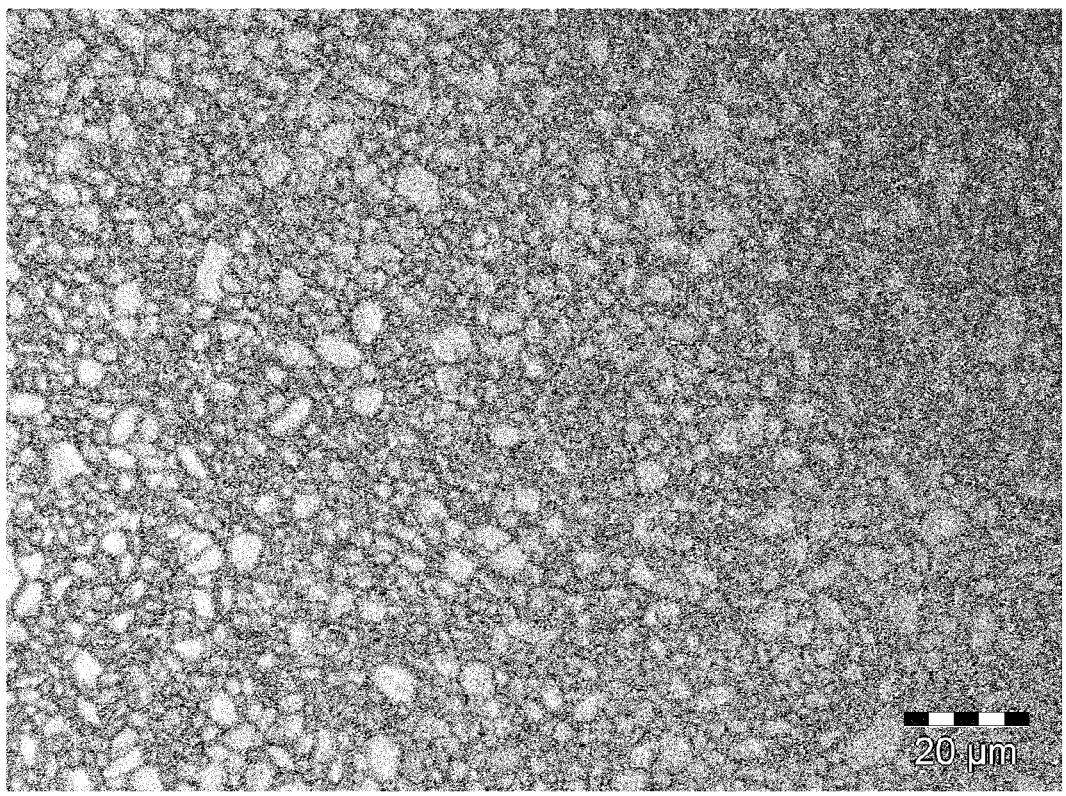
FIGS. 26A, 26B, and 26C are micrographs of polycrystalline alumina bracket material taken at a magnification of 440× in accordance with embodiments of the invention.
Figure 26B:
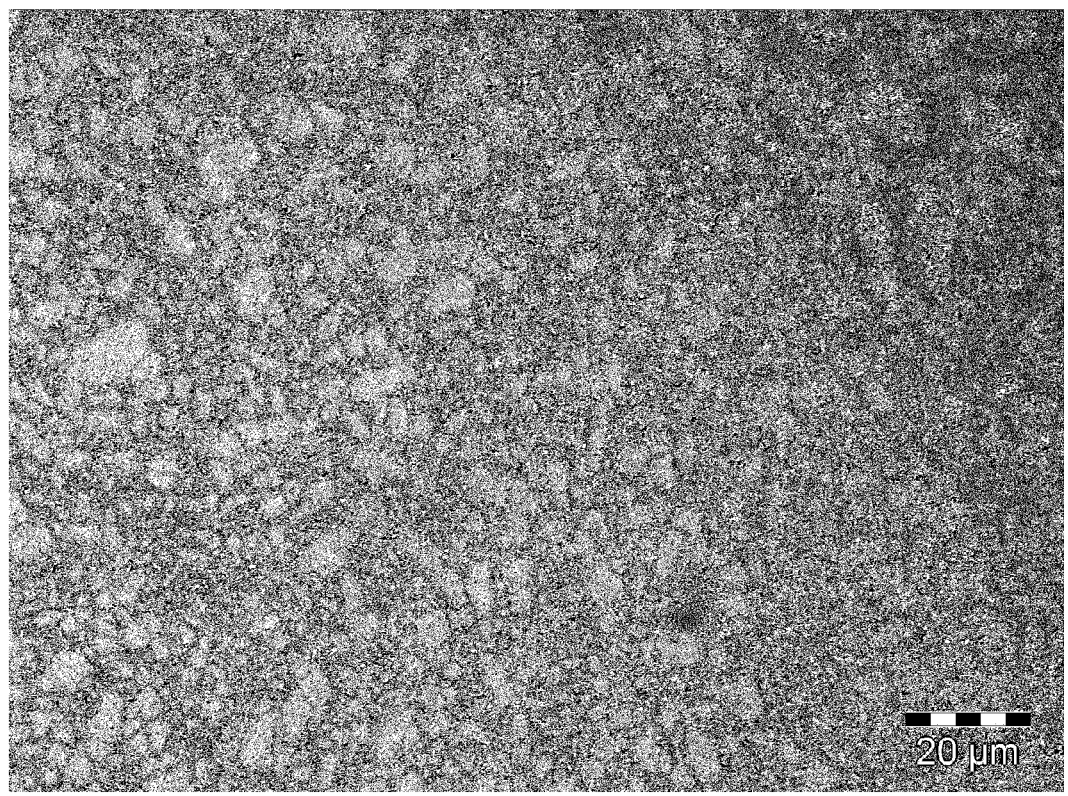

The Batch #1 samples were divided into three groups labeled Batch #1A, Batch #1B, and Batch #1C. The samples of Batch #1A and Batch #2 were not subject to further heat treatments. Exemplary micrographs for the Batch #1A and Batch #2 samples are shown in FIGS. 26A and 26B, respectively.

Figure 26C:
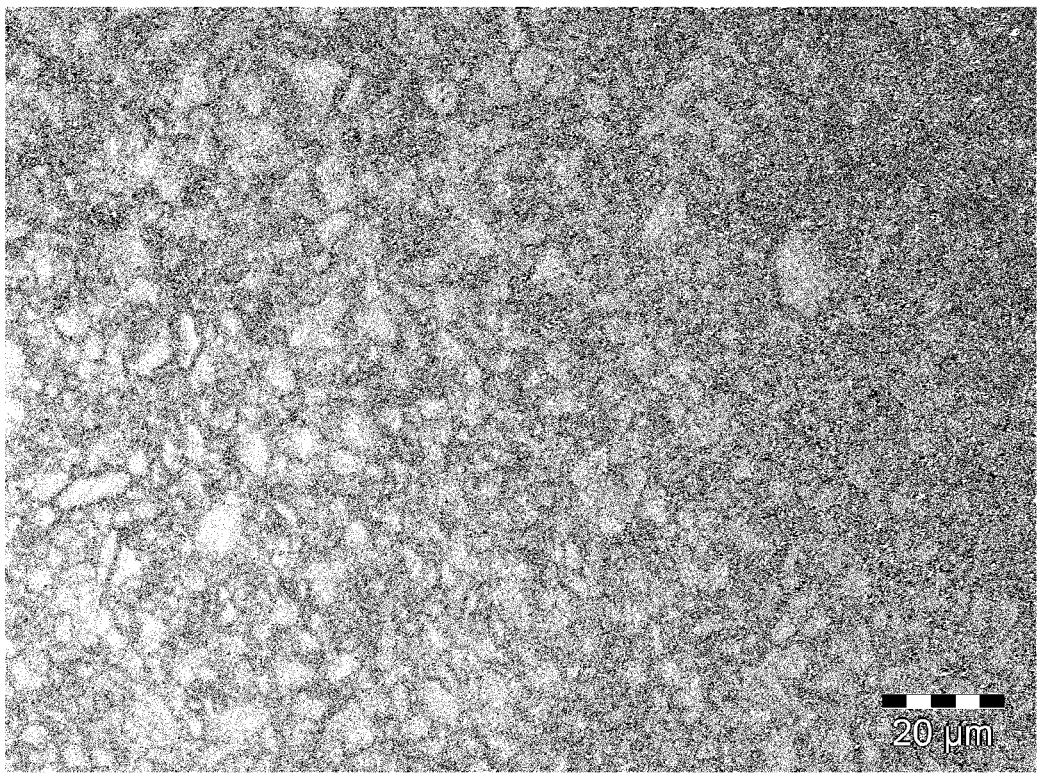

The Batch #1B samples were further heat treated in argon to a temperature of about 1,400° C. and held at that temperature for about 1 hour to modify the grain size distribution. An exemplary micrograph of a Batch #1B sample is shown in FIG. 26C.

Figure 26D:
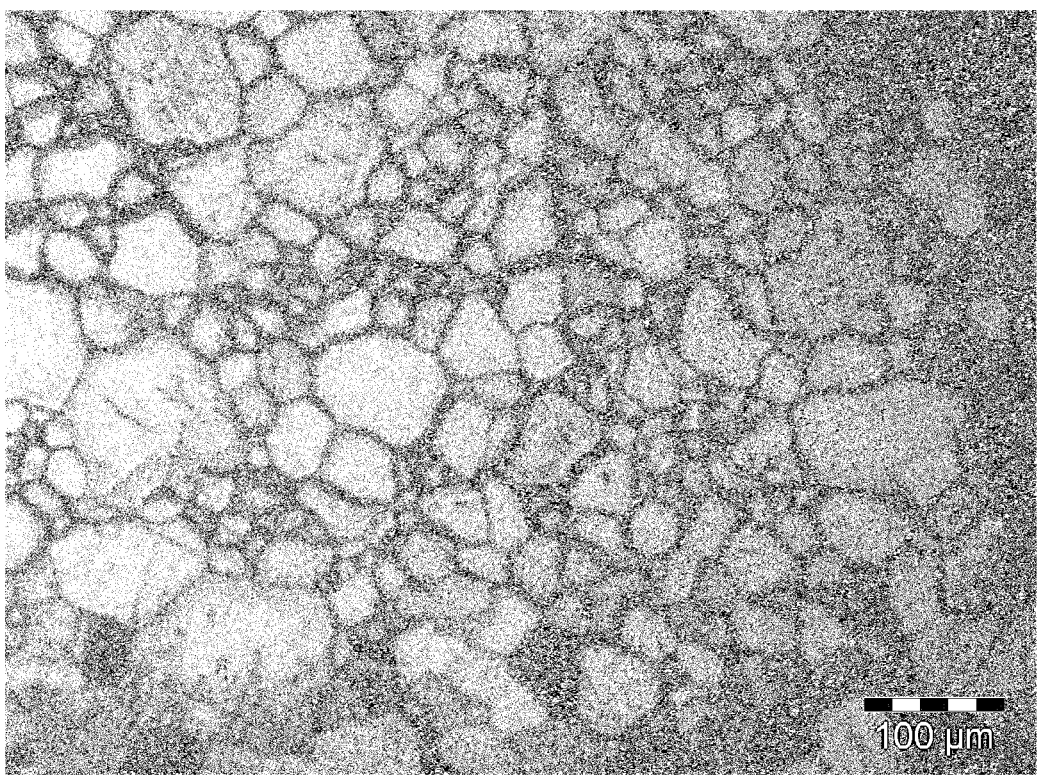
FIG. 26D is a micrograph of polycrystalline alumina bracket material taken at a magnification of 110×.

The Batch #1C samples were further heat treated in argon to a temperature of about 1,800° C. and held at that temperature for about 1 hour to modify the grain size distribution. An exemplary micrograph of a Batch #1C sample is shown in FIG. 26D.

Four samples of each group were polished for flexural strength testing, and four others were machined to form a notch therein across the width for fracture toughness testing. The notch was designed to mimic the geometry of the archwire slot in an orthodontic bracket, such as the archwire slot 16 in the orthodontic bracket 10 illustrated in FIG. 1. The dimensions of each notch were about 0.57 mm wide and between about 0.050 mm and about 0.100 mm deep. The machining produced a 0.08 mm radius along opposing edges at the bottom of the slot. The notch was made by machining the samples with a 240/320 mesh diamond bonded wheel.

As described above, the three-point bend setup was used to break the notched and polished samples in each group. The support span measured about 9 mm. A load was applied to each sample at a rate of about 1 mm per minute until the sample fractured. The load at fracture was used to calculate the flexural strength of the notched and unnotched or polished samples, and the fracture toughness was calculated from the load at fracture for the notched samples. For calculating the fracture toughness, the measured notch depth (from about 0.050 mm to about 0.100 mm as measured) was assumed to be the crack length or a and together with the three-point bend load at fracture or P were used to calculate $K_{IC}$ according to the equation set forth above. Table 1 provides the calculated averages for each group.

TABLE 1

| Group | Average Flexural Strength, Unnotched (MPa) | Average Flexural Strength, Notched (MPa) | Average Fracture Toughness, $K_{IC}$ ($\text{Mpa} \cdot \text{m}^{1/2}$) | Average grain size (μm) |
|---|---|---|---|---|
| Batch #1A | 614.8 ± 88.0 | 220.2 ± 44.4 | 2.93 ± 0.59 | 3.4 ± 0.3 |
| Batch #2 | 563.0 ± 106.2 | 291.3 ± 32.3 | 3.85 ± 0.43 | 4.1 ± 0.5 |
| Batch #1B | 627.9 ± 64.7 | 325.5 ± 39.5 | 4.3 ± 0.54 | 4.5 ± 0.4 |
| Batch #1C | 384.0 ± 66.7 | 248.3 ± 39.5 | 3.28 ± 0.42 | 43.0 ± 11.0 |

Table 1 also provides the average grain size for each group of samples, as set forth above. To measure grain size, samples were prepared by standard polishing and etching techniques known in the art. Five representative micrographs were taken of each sample at magnifications of between about 110× to about 440×. Ten 6-inch lines were drawn on each micrograph. The intersections between each line and the grain boundaries were counted. The length of each line was divided by the number of grain boundary intersections and adjusted for magnification to obtain an average length of the grains per line. According to the line intercept method described above, the grain size for each line was calculated by multiplying the average length of the grains by 1.56. The grain sizes from each line were in turn averaged to provide an average grain size per group, which is provided in Table 1. The standard deviations provided in the table represent one standard deviation.

With reference to Table 1, while both the average fracture toughness and the average flexural strength were expected to increase as average grain size is reduced, the fracture toughness was observed to drop considerably at approximately an average grain size of 3.4 μm and below. The largest fracture toughness was observed at about 4.5 μm, and at some size above that it begins to decrease. In other words, the average fracture toughness is believed to peak somewhere in the range above 3.4 μm and at or below about 6 μm, and most likely in the range of about 3.5 μm to about 5.0 μm. For example, the samples in Batch #1B (average grain size of 4.5 μm) have an average fracture toughness in excess of 4.0 MPa·m$^{1/2}$ compared to Batch #1A (average grain size of 3.4 μm) and Batch #1C (average grain size of 43.0 μm), which have an average fracture toughness of roughly 2.9 MPa·m$^{1/2}$ and 3.3 MPa·m$^{1/2}$, respectively. That is, the Batch #1B samples exhibited an increase in average fracture toughness of more than approximately 30% over the Batch #1C samples.

The transmittance of a sample from each of Batch #1A and Batch #1B (average grain sizes of 3.4 μm and 4.5 μm, respectively) was measured with diffused visible light per ASTM E 1348-02. The transmittance was measured on a BYK-Gardner, TCS Plus, Model 8870 with D56 diffuse light taken at 100. The samples were disks of 20 mm in diameter. The disks were prepared by grinding opposing sides of the disks to obtain a thickness of 1 mm, and, subsequently, polishing the ground sides of the disk with 600 grit paper then with 3 micron diamond paste followed by 1 micron diamond paste until no scratches were visible on the polished surfaces at 200×. The sample from Batch #1A (average grain size of 3.4 μm) had a transmittance of 45%, and the sample from Batch #1C (average grain size of 43.0 μm) had a transmittance above 50%. For reference purposes, the transmittance through single crystal alumina with diffuse visible light was 85%.

In addition, bracket bodies of polycrystalline alumina from two different molds (Mold A and Mold C) were obtained from Tosoh Corporation, Tokyo, Japan. Bracket bodies from both molds were of a self-ligating bracket design.

Figure 27A:
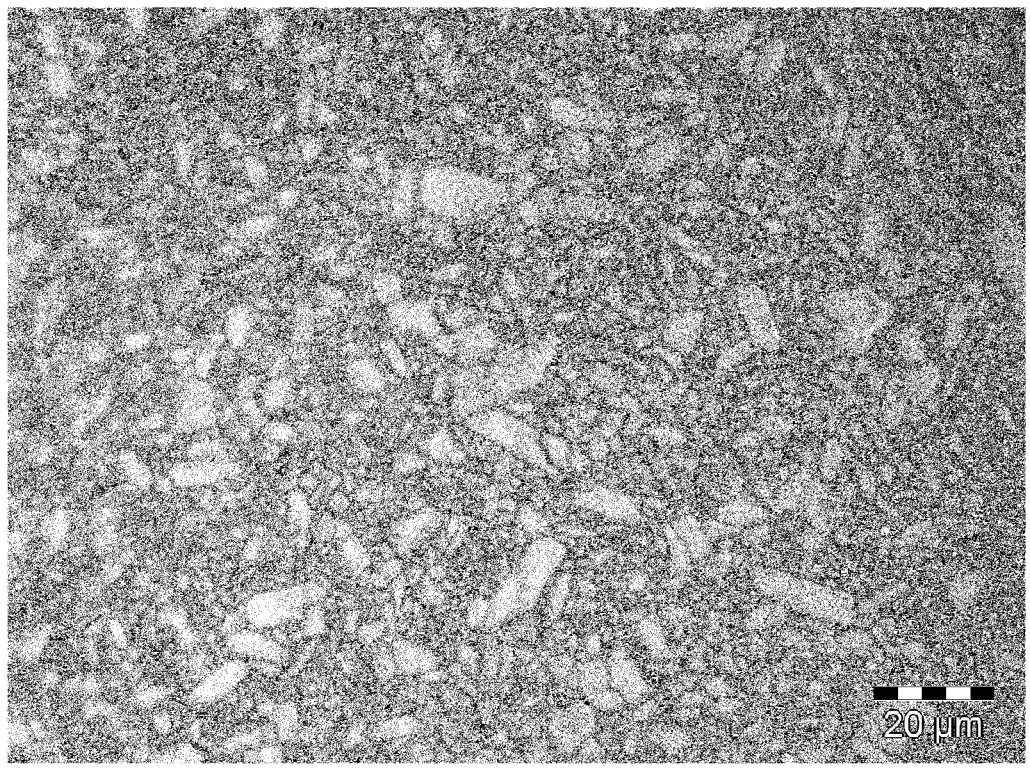
FIGS. 27A, 27B, 27C, and 27D are micrographs of polycrystalline alumina bracket material taken at a magnification of 440× in accordance with embodiments of the invention.

With reference to Table 2, below, the hardness and average grain size of five brackets from each of Mold A and Mold C were measured in the as-received condition. The "as-received" brackets are labeled Mold A(*) and Mold C(*) in Table 2. A representative micrograph of the as-received Mold C(*) microstructure (i.e., the as-received bracket) is depicted in FIG. 27A. The remaining brackets of Mold C were divided into 3 groups, each group being subject to additional heat treatment to modify their microstructures, as described below.

Figure 27B:
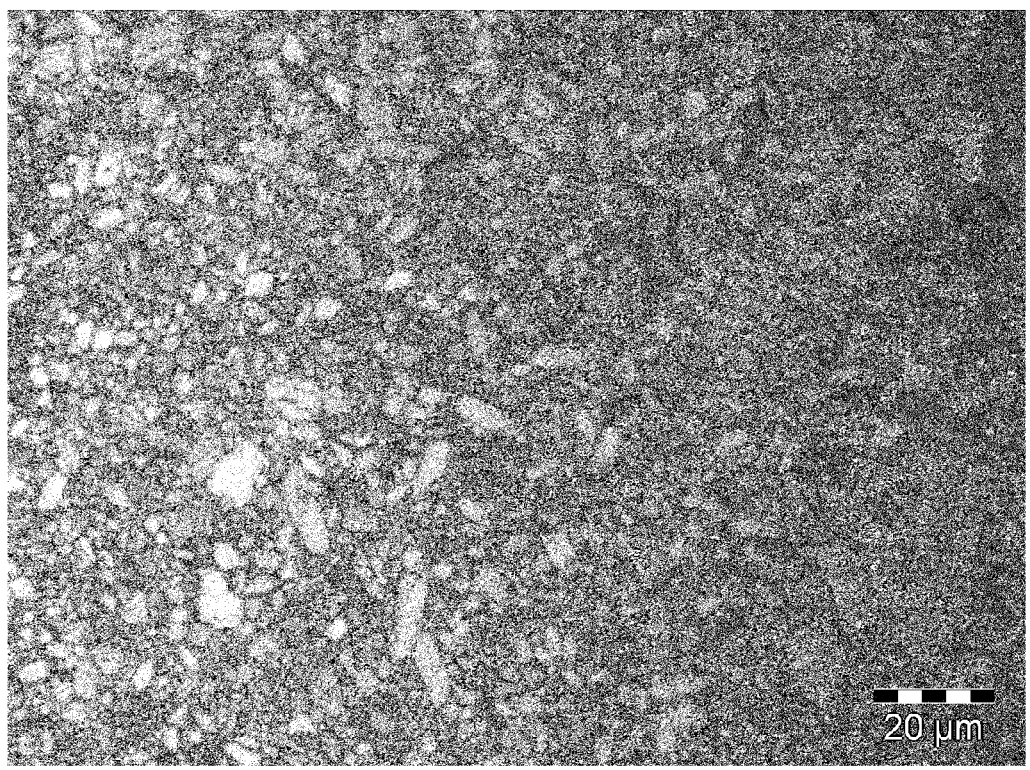

Five brackets of Mold C were subject to an additional heat treatment at a temperature of about 1,300° C. for about 1 hour in argon (Ar). This group of brackets is labeled Mold C(Ar) in Table 2. A representative micrograph of the Mold C(Ar) microstructure is depicted in FIG. 27B.

Figure 27C:
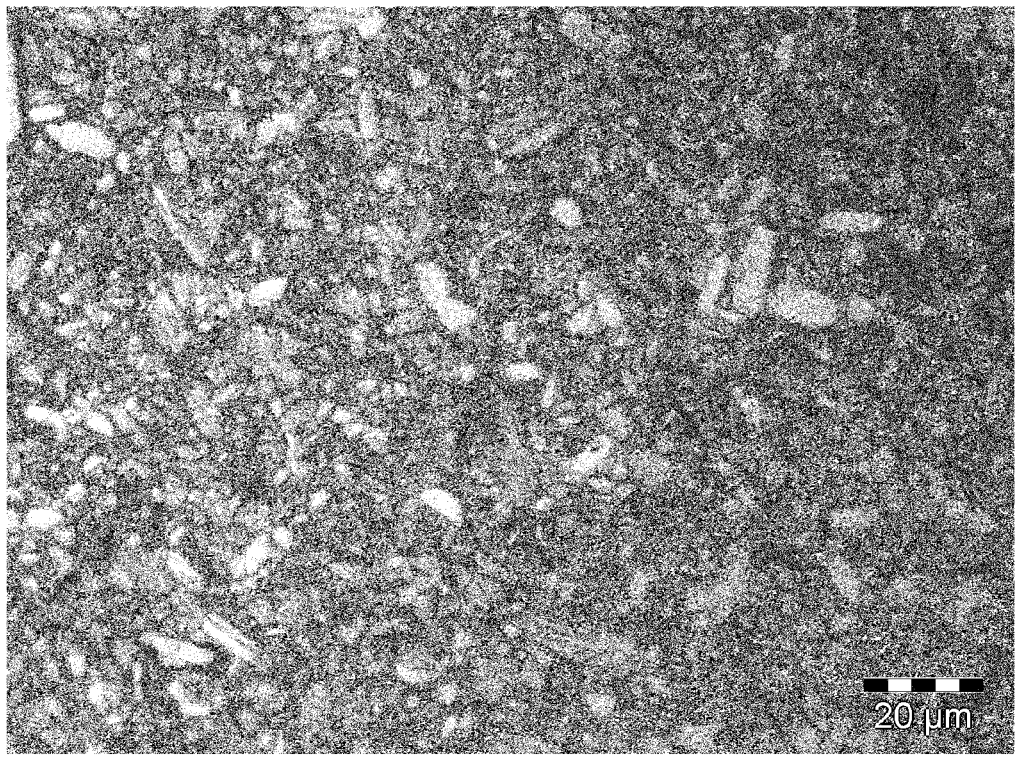

Five brackets were further heat treated at a temperature of about 1,300° C. for about 1 hour in hydrogen ($H_2$). This group of brackets is labeled Mold C($H_2$) in Table 2. A representative micrograph of the Mold C($H_2$) microstructure is depicted in FIG. 27C.

Figure 27D:
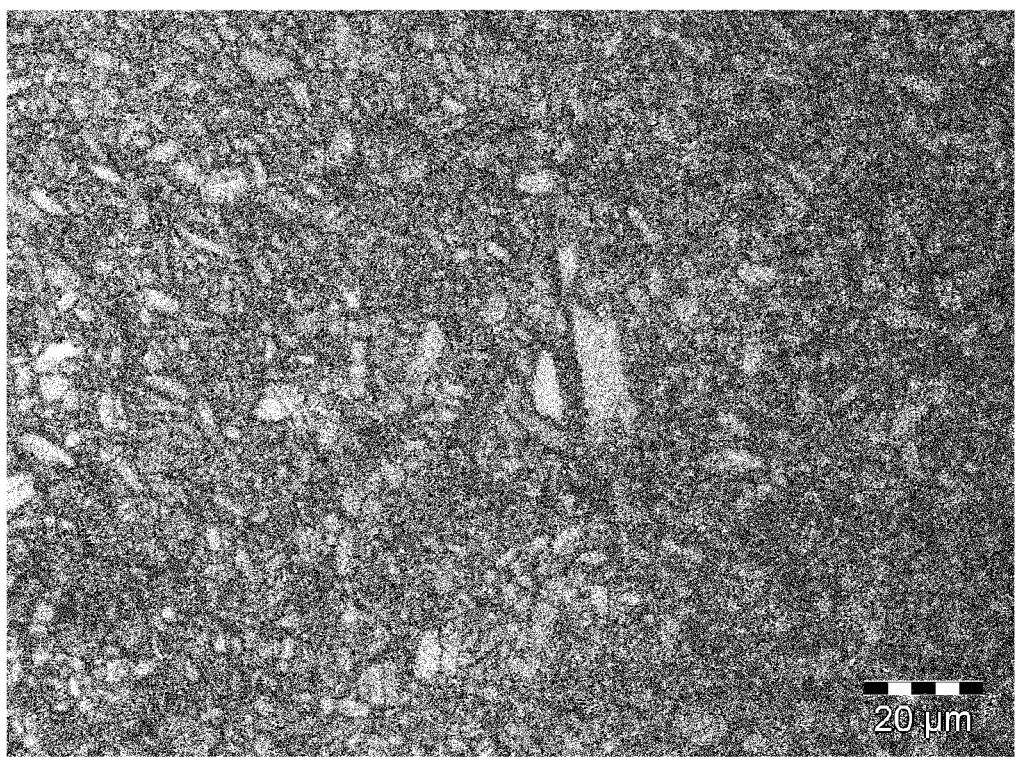

Five brackets were further heat treated at a temperature of about 1,300° C. for about 1 hour in oxygen ($O_2$). This group of brackets is labeled Mold C($O_2$) in Table 2. A representative micrograph of the Mold C($O_2$) microstructure is depicted in FIG. 27D.

The hardness and the average grain size of each bracket of each group were measured according to the procedures outlined above. The average fracture toughness was calculated based on the Vickers hardness measurement according to the equation set forth above.

Table 2 lists the average Vickers Hardness, average fracture toughness, and the average grain size of all of the Mold A and Mold C brackets segregated by heat treatments, described above. The deviation provided for each of the average fracture toughness and the average grain size represents one standard deviation.

TABLE 2

| Group | Hardness (HV) | Average Fracture Toughness, $K_{IC}$ (Mpa·m$^{1/2}$) | Average grain size (μm) |
|---|---|---|---|
| Mold C(*) | 1714 ± 92 | 4.01 ± 0.56 | 3.5 ± 0.4 |
| Mold C(Ar) | 1721 ± 124 | 4.81 ± 0.69 | 3.6 ± 0.3 |
| Mold C($O_2$) | 1660 ± 30 | 5.57 ± 0.16 | 4.0 ± 0.5 |
| Mold C($H_2$) | 1734 ± 56 | 5.35 ± 0.91 | 4.3 ± 0.5 |
| Mold A(*) | 1644 ± 54 | 4.3 ± 1.0 | 5.0 ± 0.7 |

As shown in Table 2, the average fracture toughness of the brackets has a similar trend to that illustrated in the polycrystalline alumina samples of Table 1 where the highest hardness and fracture toughness is observed for an average grain size between about 4.0 μm and about 4.3 μm. By way of example, the average fracture toughness calculated according to the hardness method reaches an average of nearly 5.6 MPa·m$^{1/2}$ at an average grain size of about 4.0 μm (Mold C ($O_2$)).

In addition and with reference to FIGS. 27A-27D, the microstructure of the polycrystalline ceramic is a mixture of very small grains and large grains. The grain sizes of the distributions for each of the microstructures of FIGS. 27A-27D were measured with analySIS software available from Olympus America Inc., Center Valley, Pa., using the grain size module. The distributions of the grain sizes measured with the analySIS software for the microstructures depicted in FIGS. 27A-27D are depicted in the graphs of FIGS. 28A-28D, respectively.

Figure 28A:
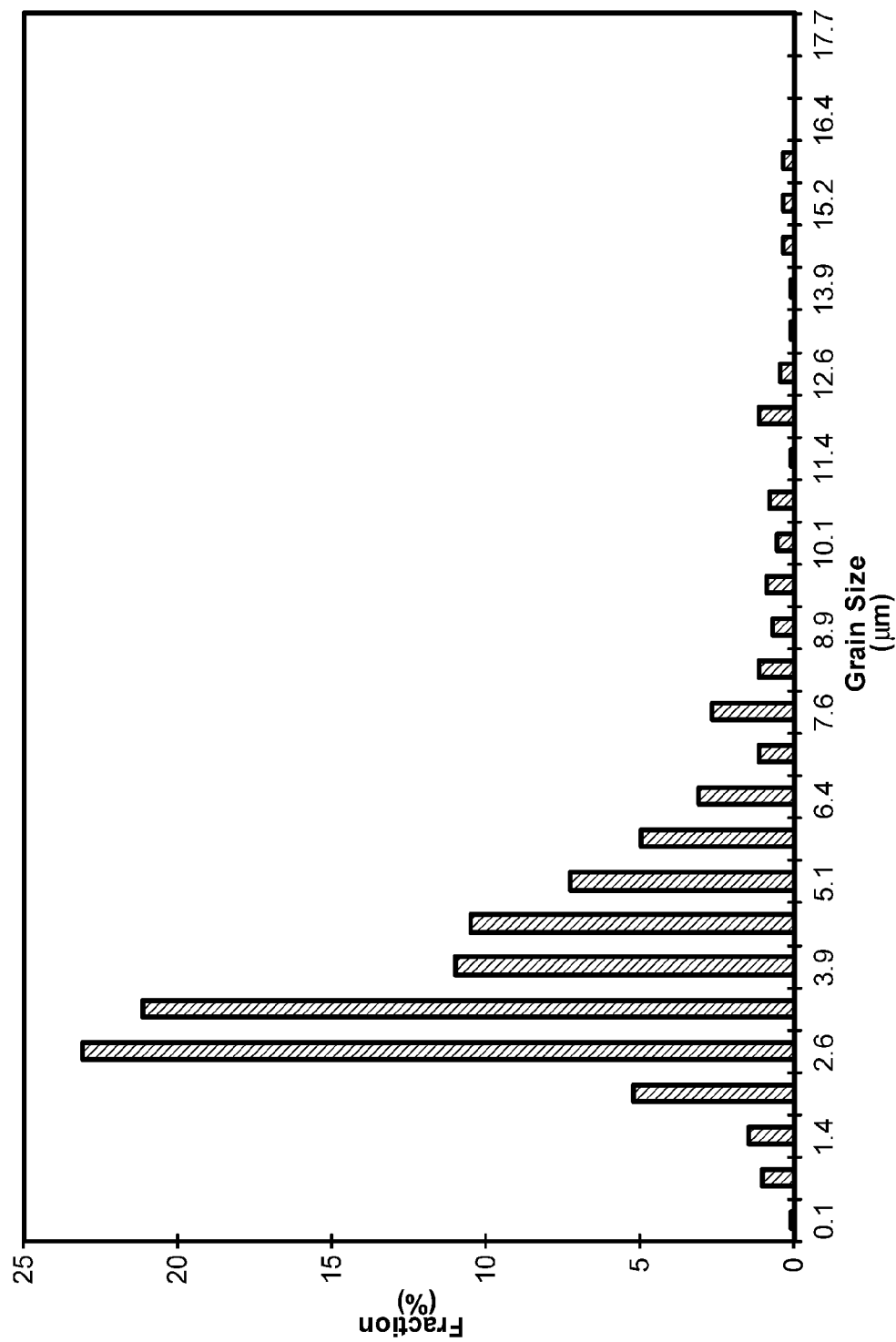
FIGS. 28A, 28B, 28C, and 28D are graphs depicting grain size distributions of the microstructures depicted in FIGS. 27A, 27B, 27C, and 27D, respectively.
Figure 28B:
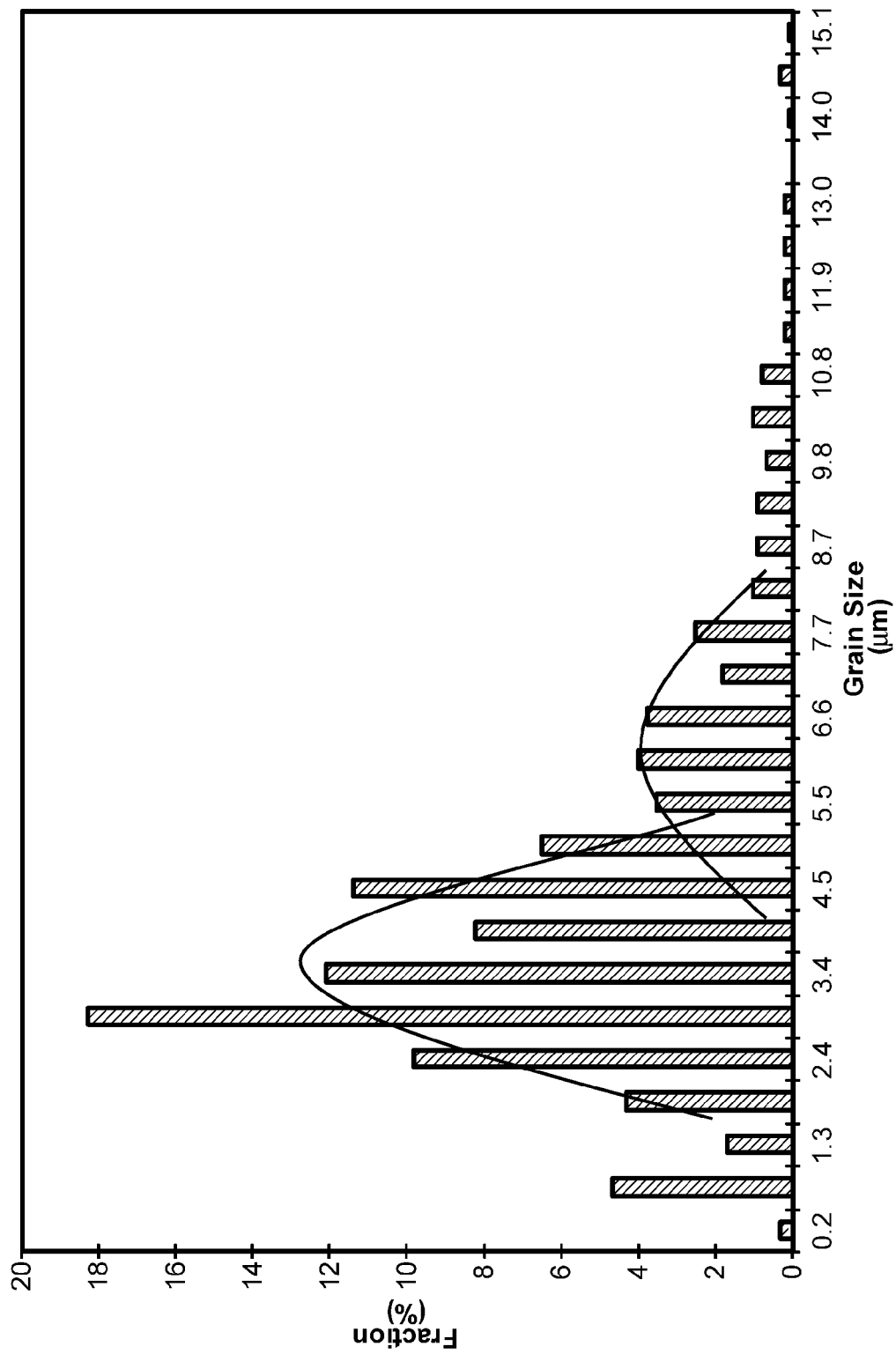
Figure 28C:
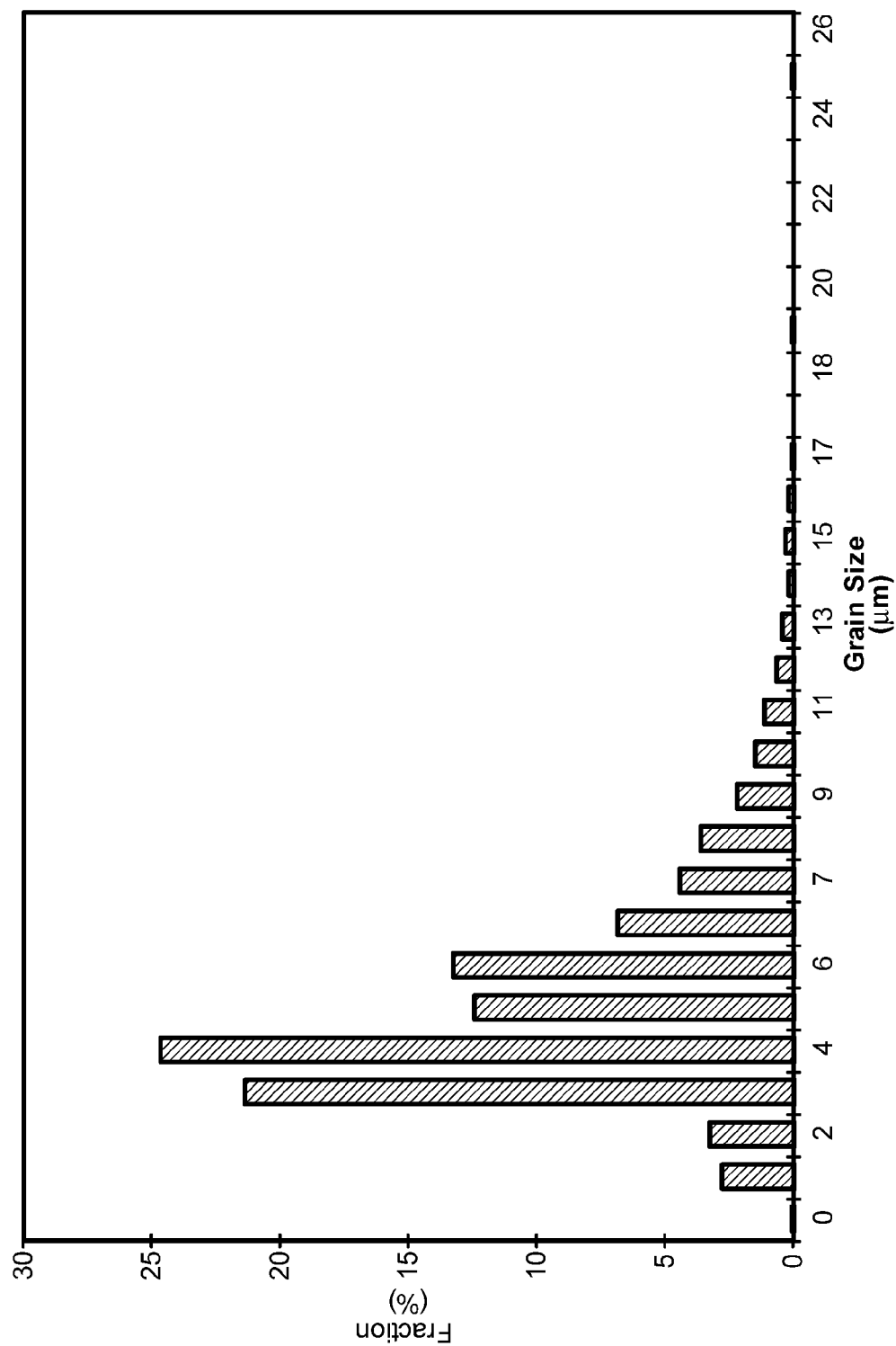
Figure 28D:
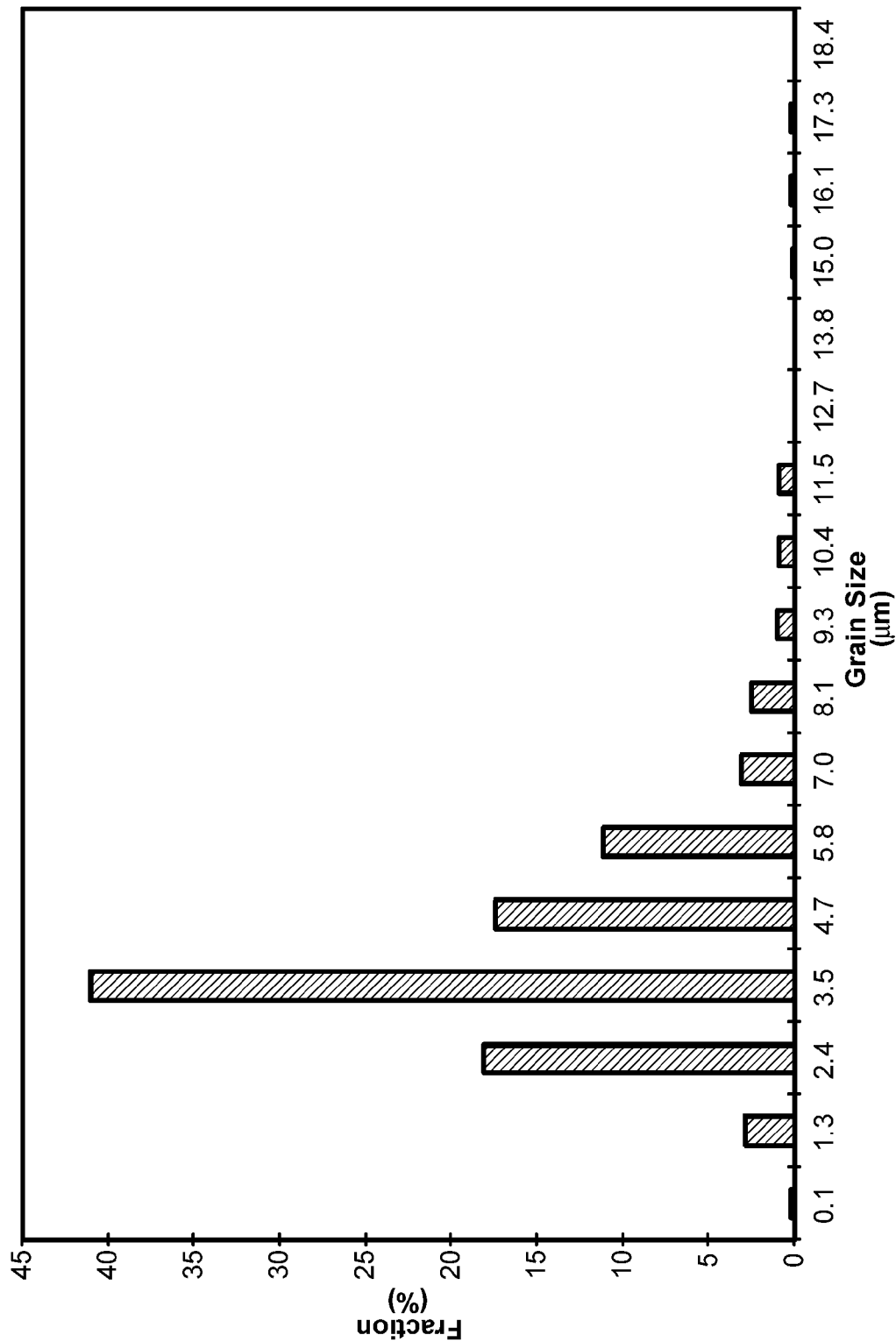

As shown in FIGS. 28A-28D, the grain size distributions contain grain sizes smaller than 3.4 μm and grains larger than 6 μm. For example, FIG. 28A depicts a grain size distribution having an average grain size of about 3.5 μm and having about 31% of the total number of grains less than about 3 μm, and, in a further example, FIG. 28B depicts a grain size distribution having an average grain size of about 3.6 μm and having about 39% of the total number of grains less than about 3 μm.

With particular reference to FIG. 28B, two curves have been provided to more clearly illustrate a bimodal grain size distribution. One of the modes is located at about 3.4 μm. The other or second mode is located at about 6.0 μm.

Figure 29:
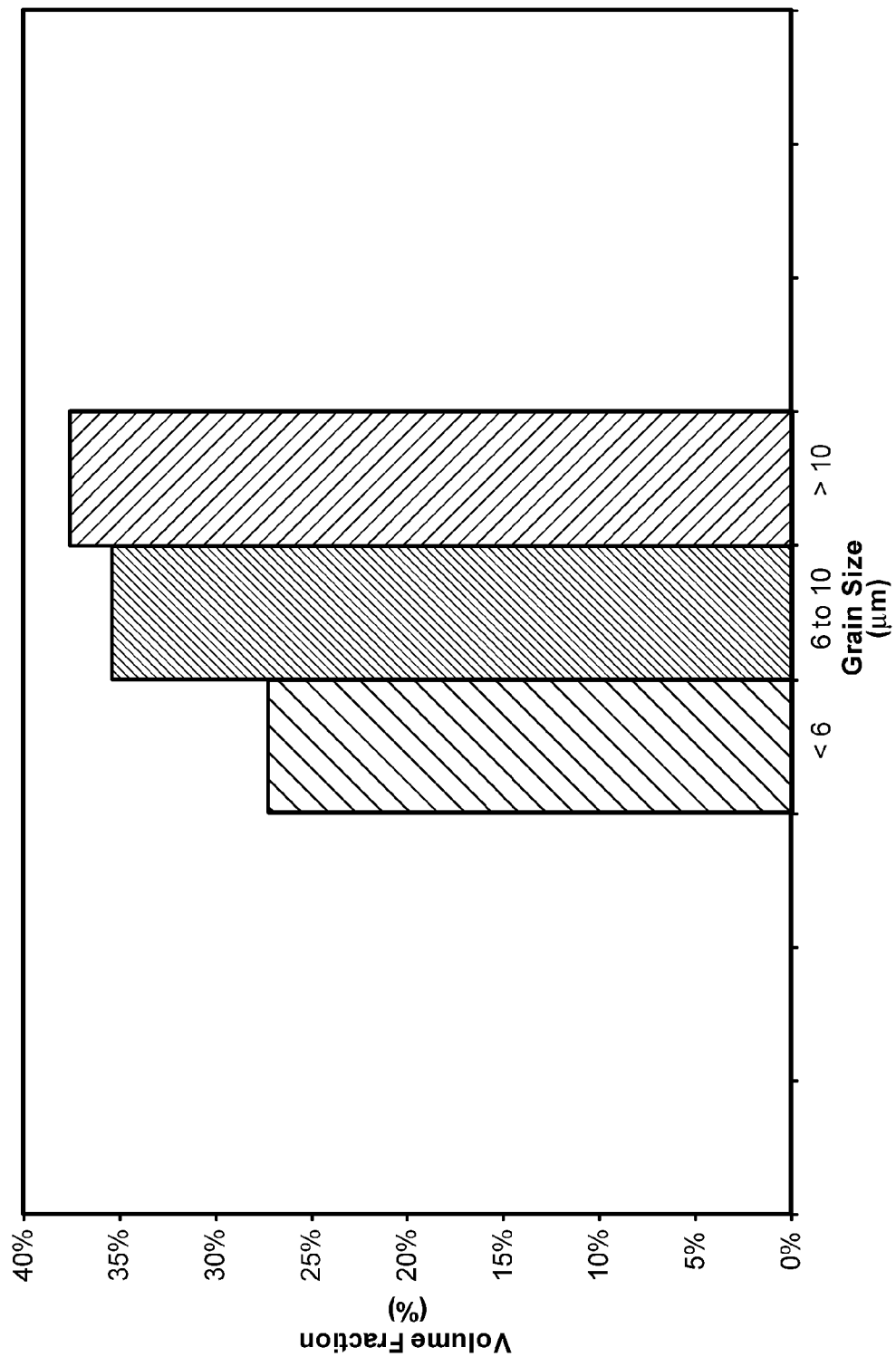
FIG. 29 is a graph of the calculated volume fraction for three grain size ranges for the microstructure depicted in FIG. 27B in accordance with one embodiment of the invention.
Figure 30:
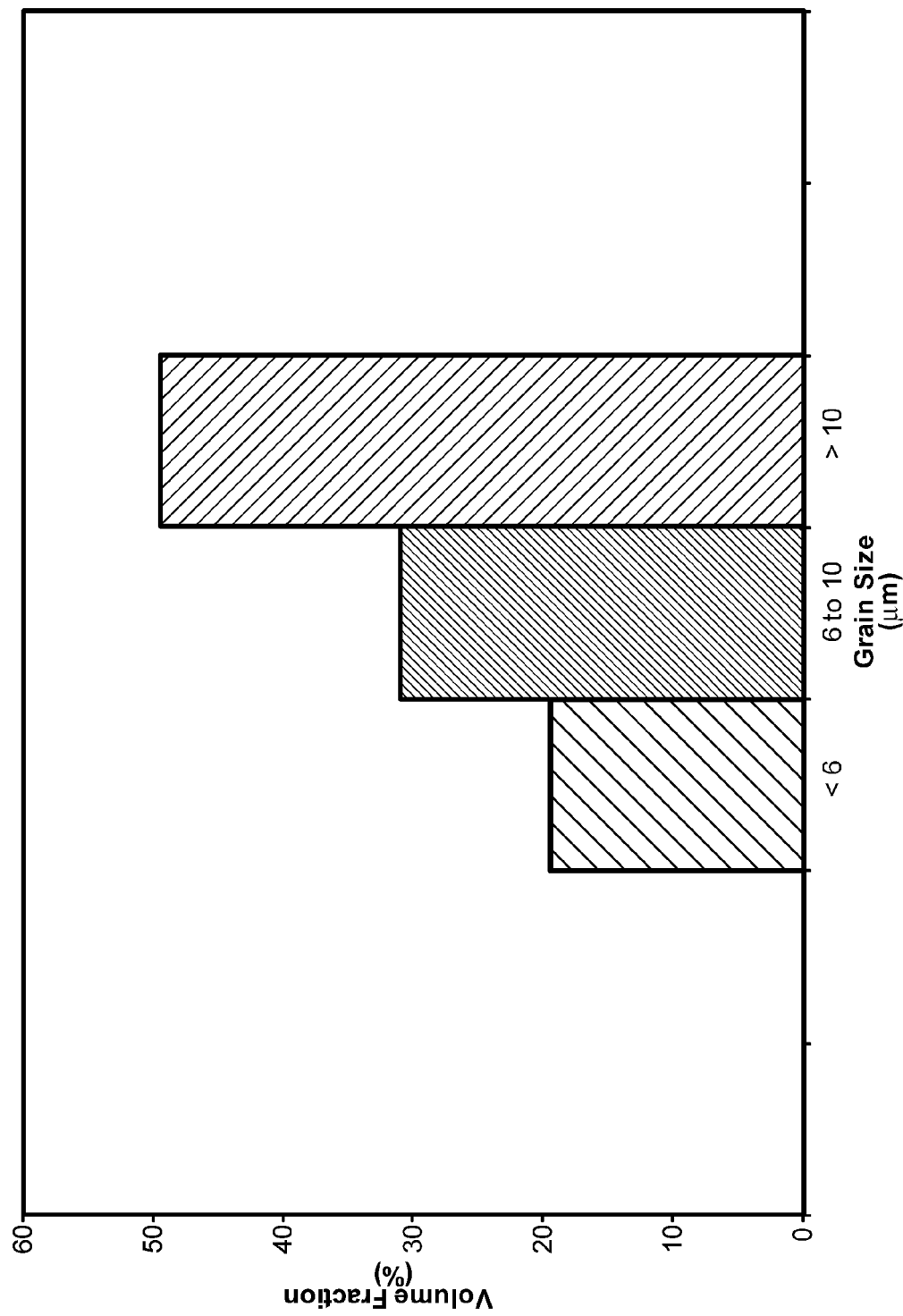
FIG. 30 is a graph of the calculated volume fraction for three grain size ranges for the microstructure depicted in FIG. 27C in accordance with one embodiment of the invention.

FIGS. 29 and 30 are graphs depicting volume fraction of grains based on calculations made from the grain size distributions depicted in FIGS. 27B and 27C, respectively. With reference to FIG. 29, by way of example, about 37% of the total volume of the grains is occupied by grains that have a size larger than 10 μm. With reference to FIG. 30, by way of another example, grains larger than 10 μm in size occupy about 50% of the total volume.

While the present invention has been illustrated by a description of various preferred embodiments and while these embodiments have been described in some detail, it is not the intention of the inventors to restrict or in any way limit the scope of the appended claims to such detail. Thus, additional advantages and modifications will readily appear to those skilled in the art. The various features of the invention may be used alone or in any combination depending on the needs and preferences of the user.

What is claimed is:

1. An orthodontic bracket for coupling an archwire with a tooth, comprising:
    a bracket body configured to be mounted to the tooth, including an archwire slot configured to receive the archwire therein, the bracket body comprising a polycrystalline alumina having a plurality of grains, adjacent grains being separated by a grain boundary, and having a grain size distribution for the plurality of grains characterized by an average grain size in the range above 3.4 μm and at or below about 6 μm; wherein grains larger than 10 μm in size in the plurality of grains occupy from about 10% up to about 50% of the volume of the bracket body.

2. The orthodontic bracket of claim 1 wherein the average grain size is between about 3.5 μm and about 5 μm.

3. The orthodontic bracket of claim 1 wherein the average grain size is between about 4 μm and about 4.3 μm.

4. The orthodontic bracket of claim 1 wherein the polycrystalline alumina has a fracture toughness of at least 4.0 MPa·m$^{1/2}$.

5. The orthodontic bracket of claim 1 wherein the polycrystalline alumina has a fracture toughness of at least 5.0 MPa·m$^{1/2}$.

6. The orthodontic bracket of claim 1 wherein the grain size distribution is not characterized as a lognormal distribution.

7. The orthodontic bracket of claim 1 wherein the grain size distribution is multimodal.

8. The orthodontic bracket of claim 1 wherein the grain size distribution is bimodal.

9. The orthodontic bracket of claim 8 wherein the bimodal grain size distribution has a first peak in grain size between about 1 μm and about 5.5 μm and a second peak in grain size at a grain size greater than about 5.5 μm.

10. The orthodontic bracket of claim 9 wherein the second peak is at a grain size between greater than about 5.5 μm and about 7 μm.

11. The orthodontic bracket of claim 1 wherein between about 10% and about 50% of the plurality of grains are less than about 3 μm in size.

12. The orthodontic bracket of claim 1 wherein between about 70% and about 90% of the plurality of grains are less than about 10 μm in size.

13. The orthodontic bracket of claim 1 further comprising: a ligating slide comprising the polycrystalline alumina.

14. The orthodontic bracket of claim 1 wherein, the archwire slot is embedded within the polycrystalline alumina of the bracket body, the archwire being configured to contact the polycrystalline alumina of the bracket body when the archwire is inserted therein.

15. An orthodontic bracket for coupling an archwire with a tooth, comprising:
a bracket body configured to be mounted to the tooth, including an archwire slot configured to receive the archwire therein, the bracket body comprising a polycrystalline alumina having a plurality of grains, adjacent grains being separated by a grain boundary, and having a grain size distribution for the plurality of grains characterized by an average grain size in the range of about 3.5 μm to about 5 μm, by having up to about 50% of the plurality of grains being less than about 3 μm in size, by having up to about 90% of the plurality of grains being less than about 10 μm in size, and by having grains in the plurality of grains larger than 10 μm in size occupying from about 10% up to about 50% of the volume of the bracket body, the polycrystalline alumina having a fracture toughness of at least 4.0 MPa·m$^{1/2}$.

16. An orthodontic bracket for coupling an archwire with a tooth, comprising:
a bracket body configured to be mounted to the tooth, including an archwire slot configured to receive the archwire therein, the bracket body comprising a polycrystalline alumina having a plurality of grains, adjacent grains being separated by a grain boundary, and having a grain size distribution for the plurality of grains characterized by an average grain size in the the range above 3.4 μm and at or below about 6 μm; wherein the grain size distribution is bimodal and wherein the bimodal grain size distribution has a first peak in grain size between about 1 μM and about 5.5 μm and a second peak in grain size at a grain size greater than about 5.5 μm.

* * * * *